US007105547B2

(12) United States Patent
Gordeev et al.

(10) Patent No.: US 7,105,547 B2
(45) Date of Patent: Sep. 12, 2006

(54) ANTIMICROBIAL 1-ARYL DIHYDROPYRIDONE COMPOUNDS

(75) Inventors: Mikhail Fedor Gordeev, Castro Valley, CA (US); Upinder Singh, Freemont, CA (US); Dinesh Vinoobhai Patel, Fremont, CA (US); Paul Dennis May, Kalamazoo, MI (US)

(73) Assignee: Pharmacia and Upjohn Company, Kalamazoo, MI (US)

( * ) Notice: Subject to any disclaimer, the term of this patent is extended or adjusted under 35 U.S.C. 154(b) by 103 days.

(21) Appl. No.: 10/497,626

(22) PCT Filed: Oct. 3, 2003

(86) PCT No.: PCT/IB03/04380

§ 371 (c)(1),
(2), (4) Date: Jun. 3, 2004

(87) PCT Pub. No.: WO2004/033449

PCT Pub. Date: Apr. 22, 2004

(65) Prior Publication Data

US 2005/0070580 A1    Mar. 31, 2005

Related U.S. Application Data

(60) Provisional application No. 60/417,492, filed on Oct. 10, 2002.

(51) Int. Cl.
*A61K 31/4439* (2006.01)
*C07D 413/10* (2006.01)

(52) U.S. Cl. .................. 514/340; 546/271.4
(58) Field of Classification Search ............ 546/271.4; 514/340
See application file for complete search history.

(56) References Cited

U.S. PATENT DOCUMENTS 5,668,286 A    9/1997    Yamada et al. ............ 546/209

FOREIGN PATENT DOCUMENTS

| WO | WO 93/23384 A | 11/1993 |
|----|---------------|---------|
| WO | WO 98/54161 A | 12/1998 |
| WO | WO 99/41244 A | 8/1999 |
| WO | WO 00/10566 A | 3/2000 |
| WO | WO 03/066631 A | 8/2003 |
| WO | WO 03/072553 A | 9/2003 |

OTHER PUBLICATIONS

*Approved Standard.* Methods for Dilution Antimicrobial Susceptibility Tests for Bacteria That Grow Aerobically,3$^{rd}$ ed., published 1993 by the National Committee for Clinical Laboratory Standards, Villanova, Pennsylvania, USA.
Blache, et al., *Heterocycles*, Application of the Mercuric Acetate-Edetic Acid Oxidation Method to the Synthesis of 11-Aza-1,2,3,4,5,6,7,12b-Octahydroindolo[2,3-α]Quinolizines, 1997, 45(1):57-69.
Brickner, S.J., *Current Pharmaceutical Design*, Betham Science Publishers, Schiphol, NL, Oxazolidinone Antibacterial Agents, 1996, vol. 2, 175-194. XP001007528.
Brickner, et al, *J. Med. Chem.*, Synthesis and Antibacterial Activity of U-100592 and U-100766, Two Oxazolidinone Antibacterial Agents for the Potential Treatment of Multidrug-Resistant Gram-Positive Bacterial Infections, 1996, 39:673-679.
Comins, et al., *Heterocycles*, Regio- and Stereoselective Addition of Nucleophiles to 1-Phenoxycarbonyl-2,3-Dihydropyridinium Salts, 1994, 37(2):1121-1140.
Comins, et al., *Tetrahedron Lett.*, Preparation of 2,6-Disubstituted 2,3-Dihydro-4-pyridones: Dehydrogenation of Trimethylsilyl Enol Ethers with Palladium(II) Acetate., 1995, 36(52):9449-9452.
Dehmlow, et al., *Heterocycles*, Studies Towards 3,4-Dimethoxy-1-Methyl-1,2-Dihydroxpyridine, So-Called Arecolidine, or its Tautomers, 1994, 37(1):355-366.
Diez, et al., *Heterocycles*, Preparation of a New Chiral 5,6-Dihydropyridinium Synthon, 1990, 31(3):485-492.
Dodd, et al., *Tetrahedron Lett.*, Efficient Route to the Synthesis of C-2, C-3 Substituted 4-Piperidones, 1991, 32(30):3643-3646.
Evans, et al., Tetrahedron Lett., Regioselective Preparation of α,β—Unsaturated Ketones via the Direct Dehydrogenation of Triisopropylsilyl Enol Ethers, 1995, 36(23):3985-3988.
Guerry and Neier, Chimia, Photochemical Cycloadditions to 5,6-Dihydro-4-pyridones, Oct. 1987, 41(10), 341-342.

(Continued)

*Primary Examiner*—Patricia L. Morris
(74) *Attorney, Agent, or Firm*—Lucy X. Yang

(57) ABSTRACT

The present invention provides antibacterial agents of formula I,

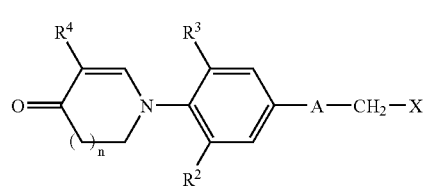

or a pharmaceutically acceptable salt thereof.

11 Claims, No Drawings

OTHER PUBLICATIONS

Guerry, et al., *Synthesis*, Reduktion von 4-Pyridinonen, 1984, 485-488.

Haider, et al., *Helv. Chim. Acta*, Synthesis of 4-Oxo-1,2,3,4-tetrahydropyridine (2,3-Dihydro-4(1H)pyridinone), 1975, 58(5):1287-1292.

Ishii, et al., *Tetrahedron Lett.*, Rhodium-Catalyzed Reaction of N-Acylpiperazines with CO and Ethylene. Carbonylation at a C-H Bond Directed by an Amido Group, 1997, 38(43):7565-7568.

Kirschbaum and Waldmann, *J. Org. Chem.*, Three-Step Access to the Tricyclic Benzo[a]quinolizine Ring System, 1998, 63:4936-4946.

Kirschbaum and Waldmann, *Tetrahedron Lett.*, Construction of the Tricyclic Benzoquinolizine Ring System by Combination of a Tandem Mannich-Michael Reaction with a Heck Reaction, 1997, 38(16):2829-2832.

Livermore, D.M., *Journal of Antimicrobial Chemotherapy*, Linezolid in vitro: mechanism and antibacterial spectrum, 2003, 51(S2):119-1116. XP002267748.

Lock and Waldmann, *Chem. Eur. J.*, Enantioselective Construction of Highly Functionalized Indoloquinolizines-Congeners to Polycyclic Indole Alkaloids, 1997, 3(1):143-151.

Lock and Waldmann, *Tetrahedron Lett.*, Asymmetric Synthesis of Highly Functionalized Tetracyclic Indole Bases Embodying the Basic Skeleton of Yohimbine- and Reserpine Type Alkaloids, 1996, 37(16):2753-2756.

Stutz and Stadler, *Tetrahedron Lett.*, A Novel Approach to Cyclic β-Carbonyl-Enamines $_\Delta^{7,8}$-Lysergic Acid Derivatives via the Polonovski Reaction, 1973, 51:5095-5098.

Waldmann, et al., *Tetrahedron*, Asymmetric Synthesis of Indolo[2,3-α]quinolizidin-2-ones-Congeners to Yohimbine-Type Alkaloids, 1993, 49(2):397-416.

ANTIMICROBIAL 1-ARYL DIHYDROPYRIDONE COMPOUNDS

CROSS REFERENCE TO RELATED APPLICATIONS

This application is filed under 35 U.S.C. 371 which is the national stage of international application PCT/IB03/04380, filed 3 Oct. 2003, which claims the benefit of U.S. provisional application Ser. No. 60/417,492, filed 10 Oct. 2002, under 35 USC 119(e)(i).

FIELD OF INVENTION

The present invention relates to novel dihydropyridone compounds and their preparations. These compounds have potent activities against Gram-positive and Gram-negative bacteria.

BACKGROUND OF THE INVENTION

The oxazolidinone antibacterial agents are a novel synthetic class of antimicrobials with potent activity against a number of human and veterinary pathogens, including Gram-positive aerobic bacteria such as multiply-resistant *staphylococci* and *streptococci*, anaerobic organisms such as *bacteroides* and *clostridia* species, and acid-fast organisms such as *Mycobacterium tuberculosis* and *Mycobacterium avium*.

However, oxazolidinones generally do not demonstrate an activity at a useful level against aerobic Gram-negative organisms. Thus, the use of these oxazolidinone antibacterial agents is limited to infectious states due to Gram-positive bacteria. Accordingly, it is among the objects of the present invention to provide pharmaceutical compounds that have broader antibacterial activity including the activity against aerobic Gram-negative organisms. We have now discovered that the oxazolidinones of the present invention increase the spectrum of activity to include gram-negative organisms such as *Haemophilus influenza* and *Moraxella catarrhalis*.

SUMMARY OF THE INVENTION

The present invention provides a compound of formula I

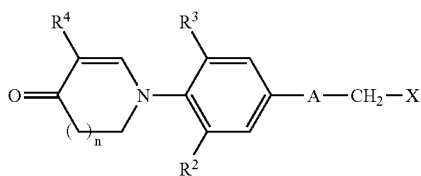

I or a pharmaceutically acceptable salt thereof wherein:
A is a structure i, ii, iii, or iv

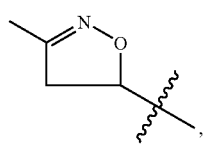

i

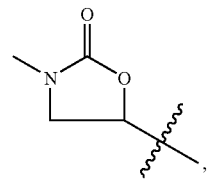

ii

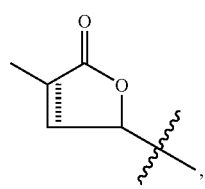

iii

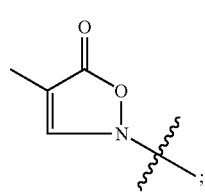

iv

X is
 (a) $NHC(=O)R^1$,
 (b) $NHC(=S)R^1$,
 (c) $NH-het^1$,
 (d) $O-het^1$,
 (e) $S-het^1$, or
 (f) $het^2$;

$R^1$ is
 (a) $NH_2$,
 (b) $NHC_{1-4}$ alkyl,
 (c) $C_{1-4}$ alkyl,
 (d) $C_{2-4}$ alkenyl,
 (e) $-(CH_2)_nC(=O)C_{1-4}$ alkyl,
 (f) $OC_{1-4}$ alkyl,
 (g) $SC_{1-4}$ alkyl, or
 (h) $(CH_2)_nC_{3-6}$ cycloalkyl;

$R^2$ and $R^3$ are independently
 (a) H,
 (b) Cl,
 (c) F,
 (d) $CH_3$,
 (e) $NH_2$, or
 (f) OH;

$R^4$ is
 (a) H,
 (b) F,
 (c) Cl,
 (d) $NH_2$,
 (e) OH,
 (f) CN,
 (g) $C_{1-4}$ alkyl,
 (h) $OC_{1-4}$ alkyl,
 (i) $C_{1-4}$ alkyl-W-$C_{1-4}$ alkyl, wherein W is O, or S,
 (j) $NHC_{1-4}$ alkyl,
 (k) $(CH_2)_nC_{3-6}$ cycloalkyl,
 (l) $C(=O)C_{1-4}$ alkyl,
 (m) $OC(=O)C_{1-4}$ alkyl,
 (n) $C(=O)OC_{1-4}$ alkyl,
 (o) $C(=O)NHC_{1-4}$ alkyl, or
 (p) $C(=O)NH_2$;

het¹ is a C-linked five (5)- or six (6)-membered heterocyclic ring having 1–4 heteroatoms selected from the group consisting of oxygen, sulfur, and nitrogen; het¹ being optionally substituted on one or more carbon atoms by 1–2 substituents selected from $C_1$–$C_4$ alkyl, amino, $C_1$–$C_4$ alkylamino, $C_1$–$C_4$ alkyloxy, halogen —CN, =O, =S, and being optionally substituted with $C_1$–$C_4$ alkyl;

het² is a N-linked five (5)- or six (6)-membered heterocyclic ring having at least one nitrogen atom, and optionally having one oxygen or sulfur atom; het² being optionally substituted on one or more carbon atoms by 1–2 substituents selected from $C_1$–$C_4$ alkyl, amino, $C_1$–$C_4$ alkylamino, $C_1$–$C_4$ alkyloxy, halogen —CN, =O, =S, and being optionally substituted with $C_1$–$C_4$ alkyl;

n is 0, 1, or 2; and at each occurrence alkyl, alkenyl, or cycloalkyl is optionally substituted with 1–3 halo, aryl, het¹, or het².

In another aspect, the present invention also provides:

a pharmaceutical composition comprising a compound of formula I or a pharmaceutically acceptable salt thereof, and a pharmaceutically acceptable carrier, a method for treating gram-positive microbial infections in a mammal by administering to the subject in need a therapeutically effective amount of a compound of formula I or a pharmaceutically acceptable salt thereof, a method for treating gram-negative microbial infections in a mammal by administering to the subject in need a therapeutically effective amount of a compound of formula I or a pharmaceutically acceptable salt thereof, and a use of a compound of formula I or a pharmaceutically acceptable salt thereof to prepare a medicament for treating gram-positive or gram-negative microbial infections.

The invention also provides some novel intermediates and processes that are useful for preparing compounds of formula I.

DETAILED DESCRIPTION OF THE INVENTION

The following definitions are used, unless otherwise described.

The term alkyl, alkenyl, etc. refer to both straight and branched groups, but reference to an individual radical such as "propyl" embraces only the straight chain radical, a branched chain isomer such as "isopropyl" being specifically referred to.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$ alkyl refers to alkyl of one to seven carbon atoms, inclusive.

The term "halo" refers to fluoro (F), chloro (Cl), bromo (Br), or iodo (I).

Aryl refers to phenyl, biphenyl, or naphthyl, optionally substituted with halo, $C_{1-4}$ alkyl, OH, $OC_{1-4}$ alkyl, CN, C(NOH)—$NH_2$, $S(O)_nC_{1-4}$ alkyl, and $NH_2$.

The term "het" encompasses both the term "het¹" and the term "het²," and is a C- or N-linked five (5)- or six (6)-membered heteroaryl ring having 1–4 heteroatoms selected from the group consisting of oxygen, sulfur, and nitrogen.

Examples of "het" include, but are not limited to, pyridine, thiophene, furan, pyrazole, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,5-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl and 5-isothiazolyl, 1,3,4,-oxadiazole, 4-oxo-2-thiazolinyl, 5-methyl-1,3,4-thiadiazol-2-yl, thiazoledione, 1,2,3,4-thiatriazole, 1,2,4-dithiazolone, 1,2,3-triazolyl, 4-cyano-1,2,3-triazolyl, 4-amino-1,2,3-triazolyl, 4-chloro-1,2,3-triazolyl, 4-hydroxy-1,2,3-triazolyl, or 4-mercapto-1,2,3-triazolyl.

"A pharmaceutically acceptable salt" refers to those salts which possess the biological effectiveness and properties of the parent compound and which are not biologically or otherwise undesirable.

"Mammal" refers to human and animals. Animals specifically refer to, for example, food animals or companion animals.

"Optionally" or "may be" means that the subsequently described event or circumstance may, but need not, occur, and that the description includes instances where the event or circumstance occurs and instances in which it does not.

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims includes both one and more than one such carrier.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

Specifically, alkyl denotes both straight and branched groups; but reference to an individual radical such as "propyl" embraces only the straight chain radical, a branched chain isomer such as "isopropyl" being specifically referred to.

Specifically, $C_{1-4}$ alkyl can be methyl, ethyl, propyl, isopropyl, butyl, iso-butyl, sec-butyl, and their isomeric forms thereof.

Specifically, $C_{2-4}$ alkenyl can be vinyl, propenyl, allyl, butenyl, and their isomeric forms thereof; $C_{3-6}$ cycloalkyl can cyclopropyl, cyclobutyl, cyclopentyl, cyclohexyl, and their isomeric forms thereof.

Specifically, halo is fluoro (F), chloro (Cl).

Specifically, $R^1$ is $C_{1-4}$alkyl, optionally substituted with one, two or three fluoro (F), or chloro (Cl).

Specifically, $R^1$ is $CH_3$, $CHF_2$, $CF_3$, or $CHCl_2$.

Specifically, $R^1$ is —CH=CH-aryl.

Specifically, $R_1$ is —$CH_2C$(=O)$C_{1-4}$ alkyl.

Specifically, $R^2$ and $R^3$ are independently H or F.

Specifically, at least one of $R^2$ and $R^3$ is F.

Specifically, n is 1.

Specifically, $R^4$ is H.

Specifically, $R^5$ is H.

Specifically, $R^2$ and $R^3$ are independently H or F; and $R^4$ is H.

Specifically, het is isoxazolyl, pyridyl, or 1,2,5-thiadiazol-3-yl.

Specifically, het is 1,2,3-triazolyl, 4-cyano-1,2,3-triazolyl, 4-amino-1,2,3-triazolyl, 4-chloro-1,2,3-triazolyl, 4-hydroxy-1,2,3-triazolyl, or 4-mercapto-1,2,3-triazolyl.

Specifically, het is 1,2,3-triazolyl.

Specific compounds of the present invention are those wherein structure i, ii, or iii has an optical configuration below:

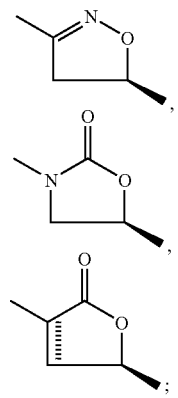

It will be appreciated by those skilled in the art that compounds of the present invention may have additional chiral centers and be isolated in optically active or racemic forms. It is to be understood that the present invention encompasses any racemic, optically-active, polymorphic, tautomeric, or stereoisomeric form, or mixture thereof, of a compound of the invention, which possesses the useful properties described herein. It being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art.

Other specific compounds of the present invention are the compounds of formula II

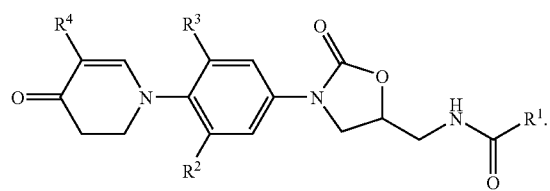

Other specific compounds of the present invention are the compounds of formula III

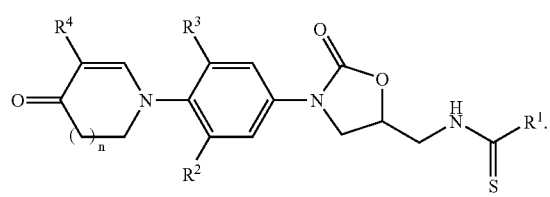

Other specific compounds of the present invention are the compounds of formula IV

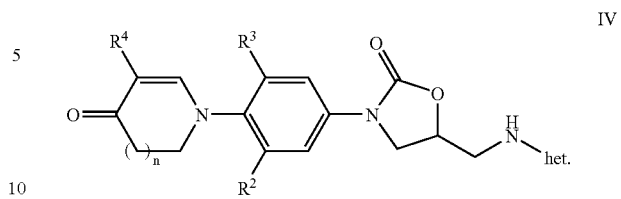

Other specific compounds of the present invention are the compounds of formula V

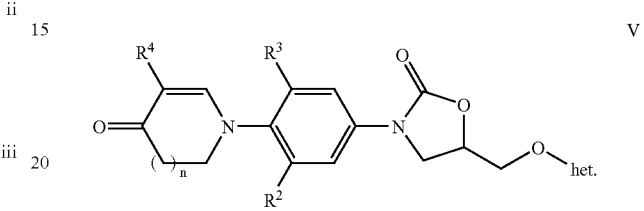

Other specific compounds of the present invention are the compounds of formula VI

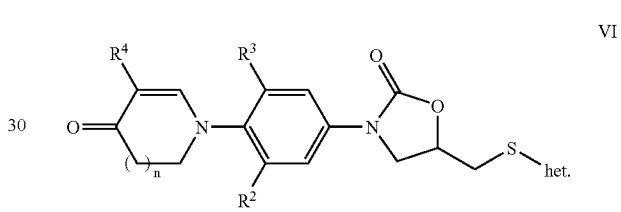

Other specific compounds of the present invention are the compounds of formula VII

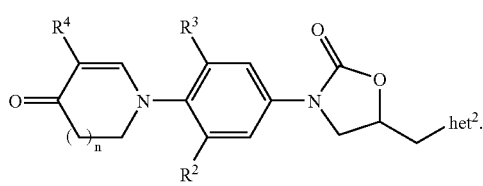

Examples of the present invention include, but are not limited to,

N-{3-[3-fluoro-4-(4-oxo-3,4-dihydro-2H-pyridin-1-yl)-phenyl]-2-oxo-oxazolidin-5-ylmethyl}-acetamide;

N-{3-[3,5-difluoro-4-(4-oxo-3,4-dihydro-2H-pyridin-1-yl)-phenyl]-2-oxo-oxazolidin-5-ylmethyl}-acetamide;

N-{3-[3-fluoro-4-(4-oxo-3,4-dihydro-2H-pyridin-1-yl)-phenyl]-2-oxo-oxazolidin-5-ylmethyl}-difluoroacetamide;

N-{3-[3-fluoro-4-(4-oxo-3,4-dihydro-2H-pyridin-1-yl)-phenyl]-2-oxo-oxazolidin-5-ylmethyl}-propionamide;

N-{3-[3,5-difluoro-4-(4-oxo-3,4-dihydro-2H-pyridin-1-yl)-phenyl]-2-oxo-oxazolidin-5-ylmethyl}-propionamide;

2,2-dichloro-N-{3-[3-fluoro-4-(4-oxo-3,4-dihydro-2H-pyridin-1-yl)-phenyl]-2-oxo-oxazolidin-5-ylmethyl}-acetamide;

2,2-difluoro-N-{3-[3-fluoro-4-(4-oxo-3,4-dihydro-2H-pyridin-1-yl)-phenyl]-2-oxo-oxazolidin-5-ylmethyl}-thio-acetamide;

{3-[3-difluoro-4-(4-oxo-3,4-dihydro-2H-pyridin-1-yl)-phenyl]-2-oxo-oxazolidin-5-ylmethyl}-carbamic acid methyl ester;

{3-[3,5-difluoro-4-(4-oxo-3,4-dihydro-2H-pyridin-1-yl)-phenyl]-2-oxo-oxazolidin-5-ylmethyl}-carbamic acid methyl ester;

{3-[2-oxo-3-[4-(4-oxo-3,4-dihydro-2H-pyridin-1-yl)-phenyl]-oxazolidin-5-ylmethyl}-carbamic acid methyl ester;

2,2-dichloro-N-{2-oxo-3-[4-(4-oxo-3,4-dihydro-2H-pyridin-1-yl)-phenyl]-oxazolidin-5-ylmethyl}-acetamide;

N-{2-dxo-3-[4-(4-oxo-3,4-dihydro-2H-pyridin-1-yl)-phenyl]-oxazolidin-5-ylmethyl}-acetamide;

2,2-difluoro-N-{2-oxo-3-[4-(4-oxo-3,4-dihydro-2H-pyridin-1-yl)-phenyl]-oxazolidin-5-ylmethyl}-thioacetamide;

N-{2-dxo-3-[4-(4-oxo-3,4-dihydro-2H-pyridin-1-yl)-phenyl]-oxazolidin-5-ylmethyl}-propionamide;

N-{3-[3,5-difluoro-4-(4-oxo-3,4-dihydro-2H-pyridin-1-yl)-phenyl]-2-oxo-oxazolidin-5-ylmethyl}-2,2-difluoro-acetamide;

N-{3-[3,5-difluoro-4-(4-oxo-3,4-dihydro-2H-pyridin-1-yl)-phenyl]-2-oxo-oxazolidin-5-ylmethyl}-2,2-difluoro-thioacetamide;

N-{3-[3-fluoro-4-(4-oxo-3,4-dihydro-2H-pyridin-1-yl)-phenyl]-2-oxo-oxazolidin-5-ylmethyl}-2,2-difluoro-thioacetamide;

2,2-dichloro-N-{3-[3,5-difluoro-4-(4-oxo-3,4-dihydro-2H-pyridin-1-yl)-phenyl]-2-oxo-oxazolidin-5-ylmethyl}-acetamide;

2-chloro-2-fluoro-N-({(5S)-3-[3-fluoro-4-(4-oxo-3,4-dihydropyridin-1(2H)-yl)phenyl]-2-oxo-1,3-oxazolidin-5-yl}methyl)acetamide;

N-({(5S)-3-[3-fluoro-4-(4-oxo-3,4-dihydropyridin-1(2H)-yl)phenyl]-2-oxo-1,3-oxazolidin-5-yl}methyl)cyclopropanecarboxamide;

1-{2-fluoro-4-[(5R)-2-oxo-5-(1H-1,2,3-triazol-1-ylmethyl)-1,3-oxazolidin-3-yl]phenyl}-2,3-dihydropyridin-4(1H)-one;

N-({(5S)-3-[3-fluoro-4-(4-oxo-3,4-dihydropyridin-1(2H)-yl)phenyl]-2-oxo-1,3-oxazolidin-5-yl}methyl)-3-oxobutanamide;

1-{4-[(5R)-2-oxo-5-(1H-1,2,3-triazol-1-ylmethyl)-1,3-oxazolidin-3-yl]phenyl}-2,3-dihydropyridin-4(1H)-one;

(2E)-3-{4-[(E)-(hydroxyimino)methyl]phenyl}-N-({(5S)-2-oxo-3-[4-(4-oxo-3, 4-dihydropyridin-1 (2H)-yl)phenyl]-1,3-oxazolidin-5-yl} methyl)prop-2-enamide; or (2E)-N-({(5S)-3-[3-fluoro-4-(4-oxo-3,4-dihydropyridin-1(2H)-yl)phenyl]-2-oxo-1,3-oxazolidin-5-yl}methyl)-3-{4-[(E)-(hydroxyimino)methyl]phenyl}prop-2-enamide.

The compound of the present invention may be used in its native form or as a salt. In cases where forming a stable nontoxic salt is desired, administration of the compound as a pharmaceutically acceptable salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, ketoglutarate, and glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example by reacting a compound of the present invention with a suitable acid affording a physiologically acceptable anion.

Routes of Administration

The oxazolidinone antibacterial agents of this invention have useful activity against a variety of organisms including, but not limiting to, *Staphylococcus aureus, Staphylococcus epidermidis, Enterococcus faecium, Streptococcus pneumoniae, Streptococcus pyogenes, Enterococcus faecalis, Moraxella catarrhalis* and *H. influenzae*. In therapeutic use for treating, or combating, bacterial infections in a mammal (i.e. human and animals) a compound of the present invention or its pharmaceutical compositions can be administered orally, parenterally, topically, rectally, transmucosally, or intestinally.

Parenteral administrations include indirect injections to generate a systemic effect or direct injections to the afflicted area. Examples of parenteral administrations are subcutaneous, intravenous, intramuscular, intradermal, intrathecal, intraocular, intranasal, intravetricular injections or infusions techniques.

Topical administrations include the treatment of infectious areas or organs readily accessibly by local application, such as, for example, eyes, ears including external and middle ear infections, vaginal, open wound, skins including the surface skin and the underneath dermal structures, or other lower intestinal tract. It also includes transdermal delivery to generate a systemic effect.

The rectal administration includes the form of suppositories.

The transmucosal administration includes nasal aerosol or inhalation applications.

The preferred routes of administration are oral and parenteral.

Composition/Formulation

Pharmaceutical compositions of the present invention may be manufactured by processes well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, solutions, emulsions, gels, syrups, slurries, suspensions and the like, for oral ingestion by a patient. A carrier can be at least one substance which may also function as a diluent, flavoring agent, solubilizer, lubricant, suspending agent, binder, tablet disintegrating agent, and encapsulating agent. Examples of such carriers or excipients include, but are not limited to, magnesium carbonate, magnesium stearate, talc, sugar, lactose, sucrose, pectin, dextrin, mannitol, sorbitol, starches, gelatin, cellulosic materials, low melting wax, cocoa butter or powder, polymers such as polyethylene glycols and other pharmaceutical acceptable materials.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, di- or triglycerides. Stabilizers may be added in these formulations, also.

Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

The compounds may also be formulated for parenteral administration, e.g., by injections, bolus injection or continuous infusion. Formulations for parenteral administration may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

For injection, the compounds of the invention may be formulated in aqueous solution, preferably in physiologically compatible buffers or physiological saline buffer. Suitable buffering agents include trisodium orthophosphate, sodium bicarbonate, sodium citrate, N-methylglucamine, L(+)-lysine and L(+)-arginine.

Parenteral administrations also include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use. For suppository administration, the compounds may also be formulated by mixing the agent with a suitable non-irritating excipient which is solid at room temperature but liquid at rectal temperature and therefore will melt in the rectum to release the drug. Such materials include cocoa butter, beeswax and other glycerides.

For administration by inhalation, compounds of the present invention can be conveniently delivered through an aerosol spray in the form of solution, dry powder, or suspensions. The aerosol may use a pressurized pack or a nebulizer and a suitable propellant. In the case of a pressurized aerosol, the dosage unit may be controlled by providing a valve to deliver a metered amount. Capsules and cartridges of, for example, gelatin for use in an inhaler may be formulated containing a power base such as lactose or starch.

For topical applications, the pharmaceutical composition may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion such as suspensions, emulsion, or cream containing the active components suspended or dissolved in one or more pharmaceutically acceptable carriers. Suitable carriers include, but are not limited to, mineral oil, sorbitan monostearate, polysorbate 60, cetyl esters wax, ceteary alcohol, 2-octyldodecanol, benzyl alcohol and water.

For ophthalmic and otitis uses, the pharmaceutical compositions may be formulated as micronized suspensions in isotonic, pH adjusted sterile saline, or preferably, as solutions in isotonic, pH adjusted sterile saline, either with or without a preservative such as a benzylalkonium chloride. Alternatively, for ophthalmic uses, the pharmaceutical compositions may be formulated in an ointment such as petrolatum.

In addition to the formulations described previously, the compounds may also be formulated as depot preparations. Such long acting formulations may be in the form of implants. A compound of this invention may be formulated for this route of administration with suitable polymers, hydrophobic materials, or as a sparing soluble derivative such as, without limitation, a sparingly soluble salt.

Additionally, the compounds may be delivered using a sustained-release system. Various sustained-release materials have been established and are well known by those skilled in the art. Sustained-release capsules may, depending on their chemical nature, release the compounds for 24 hours or for up to several days.

Dosage

Pharmaceutical compositions suitable for use in the present invention include compositions wherein the active ingredients are contained in an amount sufficient to achieve the intended purpose, i.e., the treatment or prevent of infectious diseases. More specifically, a therapeutically effective amount means an amount of compound effective to prevent, alleviate or ameliorate symptoms of disease or prolong the survival of the subject being treated.

The quantity of active component, that is the compound of this invention, in the pharmaceutical composition and unit dosage form thereof may be varied or adjusted widely depending upon the manner of administration, the potency of the particular compound and the desired concentration. Determination of a therapeutically effective amount is well within the capability of those skilled in the art. Generally, the quantity of active component will range between 0.5% to 90% by weight of the composition.

Generally, an antibacterially effective amount of dosage of active component will be in the range of about 0.1 to about 400 mg/kg of body weight/day, more preferably about 1.0 to about 50 mg/kg of body weight/day. It is to be understood that the dosages may vary depending upon the requirements of each subject and the severity of the bacterial infection being treated. In average, the effective amount of active component is about 200 mg to 800 mg and preferable 600 mg per day.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

In cases of local administration or selective uptake, the effective local concentration of the drug may not be related to plasma concentration and other procedures know in the art may be used to determine the desired dosage amount.

Compounds of this invention have useful activity against a variety of organisms. The in vitro activity of compounds of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA. The activity of compounds of this invention against *Staphylococcus aureus* UC9213 (S.A.) is shown in Table 1.

TABLE 1

Antibacterial Activity Minimum Inhibitory Concentration (μg/mL).

| EXAMPLE # | SAUR 9213 MIC | SPNE 9912 MIC | HINF 30063 MIC |
|---|---|---|---|
| 1 | 2 | .25 | 4 |
| 2 | 1 | 0.5 | 8 |
| 3 | 1 | 0.25 | 2 |
| 4 | 1 | 0.5 | 2 |
| 5 | 1 | 0.25 | 1 |
| 6 | 1 | 0.125 | 4 |
| 7 | 2 | 0.5 | 8 |
| 8 | 2 | 0.25 | 2 |
| 9 | 2 | 0.5 | 4 |
| 10 | 1 | 0.25 | 4 |
| 11 | 2 | 0.5 | 4 |
| 12 | 4 | 0.5 | 4 |
| 13 | 2 | 0.25 | 8 |
| 14 | 0.5 | 0.25 | 8 |
| 15 | 2 | 0.25 | 4 |
| 16 | 1 | 0.25 | 8 |
| 17 | 1 | 1 | 8 |

The following Schemes describe the preparation of compounds of the present invention. All of the starting materials are prepared by procedures described in these schemes or by procedures that would be well known to one of ordinary skill in organic chemistry. The variables used in the Schemes are as defined below or as in the claims.

Dihydropyridone compounds can be made by variations of oxidative transformations of piperidone derivatives exemplified by the following references: Stutz et al. in Tetrahedron Lett., 1973, pp. 5095–5098; Dodd et al., Tetrahedron Lett., 1991, pp. 3643–3646; Evans et al., Tetrahedron Lett., 1995, pp. 3985–3988; Blache et al., Heterocycles, 1997, pp. 57–69; and Ishii et al., Tetrahedron Lett., 1997, pp. 7565–7568. In another embodiment, dihydropyridone compounds can be synthesized by variations of hetero Diels-Alder transformations of imine derivatives exemplified by the following publications: Diez et al., Heterocycles, 1990, p. 485; Waldmann et al., Tetrahedron, 1993, pp. 397–416; Lock et al., Tetrahedron lett., 1996, pp. 2753–2756; Kirschbaum et al., Tetrahedron Lett., 1997, pp. 2829–2832; Kirschbaum et al., Chem. Eur. J., 1997, pp. 143–151; and Kirschbaum et al., J. Org. Chem, 1998, pp. 4936–4946. In yet another embodiment, dihydropyridone compounds can be prepared by reductive transformations of pyridine and pyridone derivatives, see, e.g. references: Haider, et. al., Helv. Chim. Acta, 1975, p. 1287; Guerry et al., Synthesis, 1984, p. 485; Guerry et al., Chimia, 1987, p. 341; Comins et al., Heterocycles, 1994, pp. 1121–1140; and Dehmlow et al., Heterocycles, 1994, pp. 355–366. Optically pure material could be obtained either by one of a number of asymmetric syntheses or alternatively by resolution from a racemic mixture. It is understood that variations of the synthetic methods cited above should allow for further process optimization including but not limited to selection of alternative oxidizing and reducing reagents, or acid catalysts for hetero Diels-Alder chemistries.

Synthetic examples for producing dihydropyridone oxazolidinones are discussed below.

Scheme I below serves to illustrate one general synthesis of dihydropyridone oxazolidinone derivatives from amine compounds. In step 1 of this synthesis, a suitable aniline derivative (wherein NRR' is an oxazolidinone moiety, $NHCO_2CO_{1-8}$ alkyl, or $NO_2$) can be converted into imine compounds by reaction with an aldehyde in presence of optional organic or inorganic dehydrating agents, such as trimethyl orthoformate or molecular sieves. This reaction can be optionally performed in refluxing benzene or toluene with catalytic amounts of toluenesulfonic acid and using Dean-Stark apparatus to remove the water by-product.

In step 2 of the Scheme I, a suitable imine intermediate is reacted with an electron-rich diene compound, such as Danishefsky's diene (for $R_4$=H) to afford the key dihydropyridone structure. This transformation is preferably conducted in aprotic polar solvents such as tetrahydrofuran, ether, dioxane, or acetonitrile. It is further preferred to perform the [4+2] cycloaddition in the presence of an organic or inorganic acid catalyst, such as perchloric acid, zinc chloride, lithium or ytterbium triflates, boron trifluoride etherate, trimethylsilyl triflate, triphenylborate, or alike agents. Temperatures in the range of about −40° C. to about 20° C. are generally suitable for this reaction. As needed, the reaction may be performed in enantioselective fashion to generate either (R) or (S)-configuration at the $R_5$ substituent, e.g., using chiral zirconium catalysts as described by Kabayashi et al. in Angew. Chem., Int. Ed., 1998, vol. 37, pp. 979–981. In another embodiment, the imine intermediate can be replaced by a suitable imine precursor reagent, such as an aminal or N,O-acetal derivative (see below, Example 2; solvent and catalyst requirements are similar to that for imine cycloadditions).

The synthesis of Scheme I is then completed with a construction of the requisite oxazolidinone substituent (e.g., when NRR' is a carbamate or nitro group) using known chemistry (such as described by Brickner et al. in J. Med. Chem., 1996, vol. 39, pp. 673–679). It is further understood that the dihydropyridone syntheses described herein are generally applicable to syntheses of dihydropyridone derivatives bearing other groups in place of the oxazolidinone substituent (such as isoxazoline, isoxazolinone, or butenolide groups).

In one embodiment of the Scheme I wherein R" is a NHBoc group, the Boc-protected oxazolidinone derivatives can be deprotected to give the corresponding amines. It is convenient to remove the Boc group with hydrogen chloride in dioxane at 0° C. to 24° C.; however, other deprotection strategies can be employed. The synthesis is then completed by an acylation or thioacylation of the penultimate amine intermediate using known art. Thus, acylations can be routinely performed by reactions of the amines with carboxylic acid anhydrides or esters. These transformations are generally performed at 0° C. to 50° C. using polar solvents, such as acetonitrile, dimethylformamide, tetrahydrofuran, and methanol or mixtures thereof with optional apolar solvents, such as dichloromethane. These reactions are preferably conducted in presence of an organic or inorganic base, such as pyridine, triethylamine, or potassium carbonate. Thioacylations are prepared by allowing amine intermediates to react with dithioesters or thionoesters and a tertiary amine base such as triethylamine. In this reaction it is often convenient to employ an excess of the tertiary amine base with an amine salt prepared by Boc deprotection in step 2 without first isolating the free base. Solvents such as tetrahydrofuran, methylene chloride or preferably methanol and temperatures in the range of about 24° C. to about 50° C. can be used for this reaction. Other thiocarbonyl compounds of the Scheme I can be prepared according to the procedures disclosed in PCT International Publication WO 98/54161.

SCHEME I

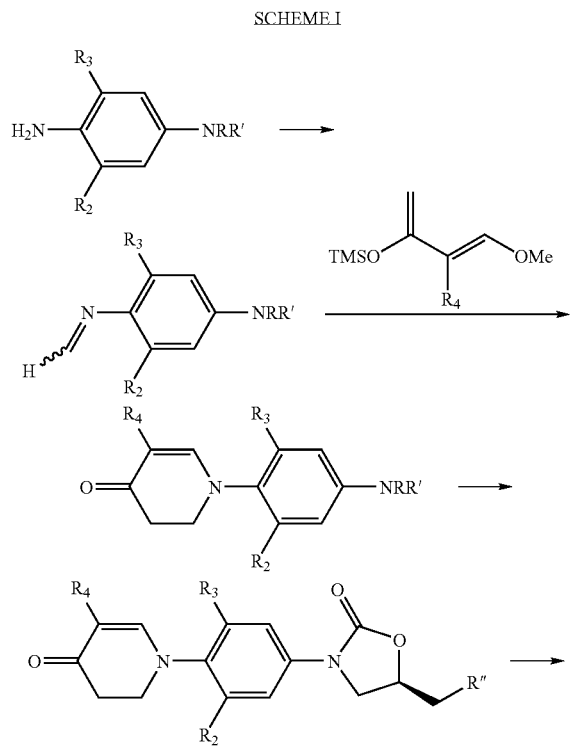

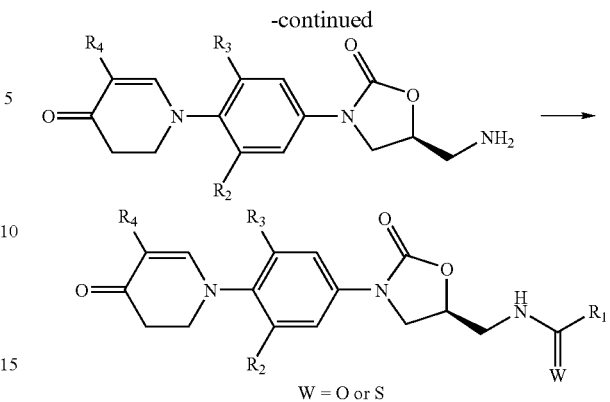

W = O or S

Scheme II serves to illustrate another general synthesis of dihydropyridone oxazolidinone derivatives from nitrobenzene and piperidine derivatives. In Scheme II, Y is a leaving group such as F, Cl, Otf, etc. Step 1 involves a nucleophilic aromatic substitution reaction of a suitable nitrobenzene with piperidine derivative, such as 4-piperidone. This reaction is performed in aprotic polar solvent such as dimethylformamide, acetonitrile, or dimethylsulfoxide in the presence of an organic or inorganic base, such as pyridine, triethylamine, or potassium carbonate. Temperatures in the range of about 20° C. to about 80° C. are generally suitable for this reaction.

Step 2 of Scheme II involves formation of a silyl enolate from the 1-arylpiperidone intermediate and a silylating agent, such as triisopropylsilyl chloride, trialkylsilyl triflate, or alike reagent (Ra is corresponding to the silylating agent being used). This reaction is typically conducted in the presence of an organic base, such as triethylamine, pyridine, or imidazole at temperatures from about 0° C. to about 60° C.

Step 3 involves an oxidation of the silyl enolate intermediates to the dihydropyridone compounds with a suitable inorganic oxidant, such as ceric ammonium nitrate (CAN; described by Evans et al. in Tetrahedron Lett., 1995, vol. 36, pp. 3985–3988) or palladium acetate (as described by Comins et al. in Tetrahedron Lett., 1995, vol. 36, pp. 9449–9452).

Subsequent oxazolidinone group construction and installation of 5-amidomethyl or 5-thioamidomethyl substituents can use the procedures as described above for Scheme I.

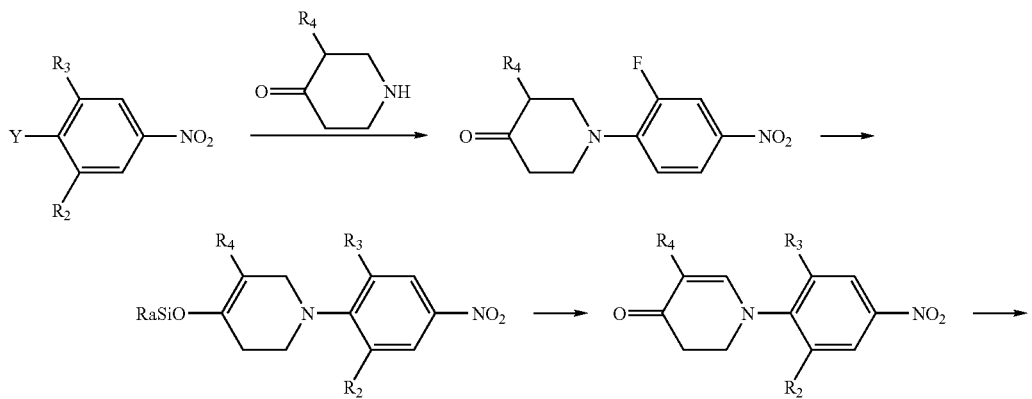

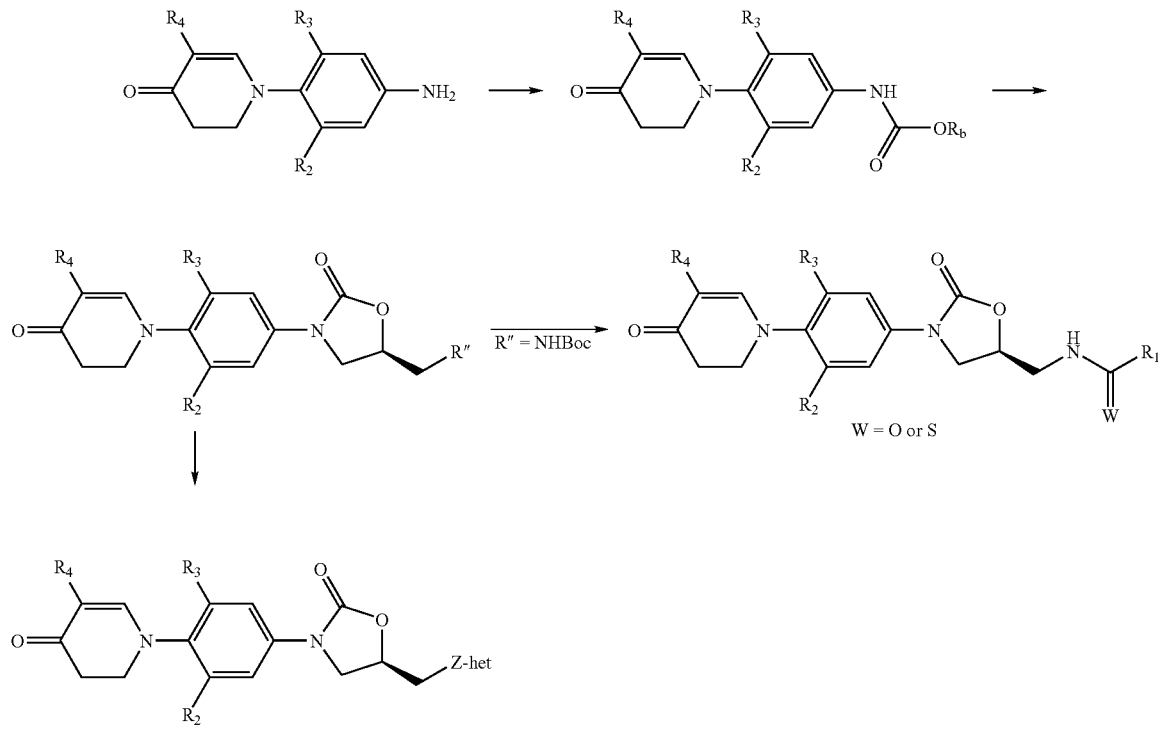

Both Schemes I and II are applicable for the introduction of 5-heteroarylaminomethyl and 5-heteroaryloxymethyl substituents from the penultimate intermediates of Schemes I or II when R″=OH and using synthetic methodology described in the PCT International applications WO 99/64417, WO 01/81350 and WO 00/21960. It should be further noted that no dihydropyridone compounds have been disclosed in the aforementioned PCT publications.

Additional syntheses of dihydropyridone compounds are illustrated by the following Examples.

EXAMPLES

Example 1

Preparation of N-{3-[3-fluoro-4-(4-oxo-3,4-dihydro-2H-pyridin-1-yl)-phenyl]-2-oxo-oxazolidin-5-ylmethyl}-acetamide

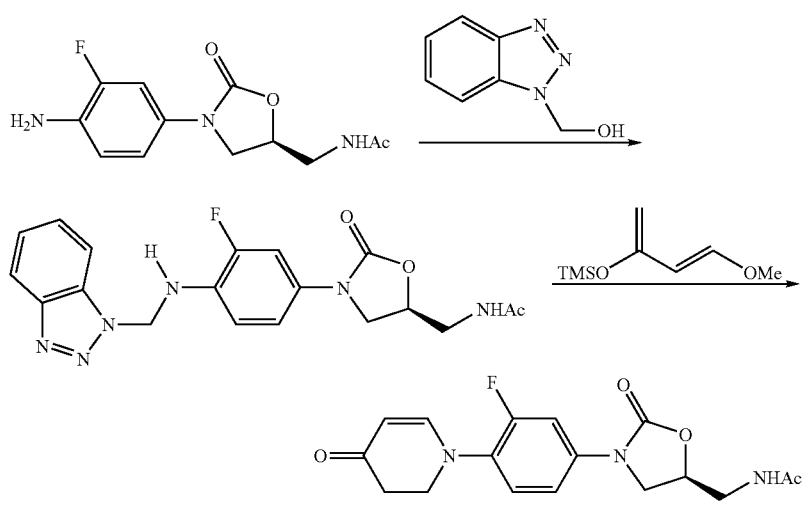

5-(S)-Acetamidomethyl-3-[4-amino-3-fluorophenyl]oxazolidine-2-one (0.250 g, 0.93 mmol), prepared as described in International Publication WO 96/23788, and hydroxymethylbenzotriazole (0.140 g, 0.93 mmol) are heated at reflux in a minimum amount of abs. EtOH (ca. 2.0 mL) until the solution turned clear. This solution is kept at r.t. for about 16 h. Precipitated white solid is filtered, washed with cold EtOH, and dried under vacuum to afford the intermediate aminal (0.362 mg, 97%).

Danishefsky's diene (0.530 mL, 2.72 mmol) is added with stirring to a suspension of aforementioned aminal intermediate (0.362 g, 0.90 mmol) in THF (2.0 mL) under nitrogen atmosphere at 0° C. BF$_3$.OEt$_2$ (1 eq.). The mixture is allowed to warm up to r.t. and stirred for another 4 h. The reaction is quenched by addition of saturated aq. NaHCO$_3$ (ca. 10 mL), and the crude material extracted with EtOAc (ca. 4×10 mL). The combined organic phase is dried over Na$_2$SO$_4$, and the solvent is removed under vacuum. The crude material is purified by silica gel column chromatography (EtOAc) followed by preparative RP HPLC (gradient 0–60% MeCN—water in 40 min) to yield the title compound. $^1$H NMR (300 MHz, CDCl$_3$) δ2.08 (s, 3H), 2.61–2.66 (m, 2H), 3.59–3.69 (m, 2H), 3.75–3.80 (m, 1H), 3.90 (t, 2H, J=7.2 Hz), 4.03 (t, 1H, J=8.7 Hz), 7.09–7.20 (m, 3H), 7.55 (dd, 1H, J=12.9 Hz, 2.55 Hz). MS (m/z): 348 [M+H]$^+$.

Example 2

Preparation of N-{3-[3,5-diluoro-4-(4-oxo-3,4-dihydro-2H-pyridin-1-yl)-phenyl]-2-oxo-oxazolidin-5-ylmethyl}-acetamide Step 1. Preparation of 2,6-difluoro-4-isopropoxycarbonylamino-benzoic Acid Tert-butyl Ester.

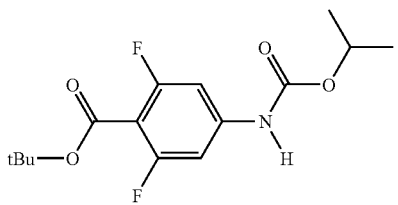

1.0 M Isopropyl chloroformate in toluene (93.0 mL, 93.0 mmol) is added dropwise with stirring to a mixture of 3,5-difluoroaniline (6.00 g, 46.47 mmol) and K$_2$CO$_3$ (16.0 g, 116.18 mmol) in anhydrous THF (25 mL). This mixture is stirred for 16 h. Ether (ca. 200 mL) is added, and the mixture is washed with 1N HCl, water, saturated aq. NaHCO$_3$, and brine. The organic phase is dried over Na$_2$SO$_4$, and the solvent is removed under vacuum. The crude product is purified by silica gel column chromatography (eluent—5% EtOAc in hexane) to afford the intermediate N-isopropylcarbamoyl-3,5-difluoroaniline. $^1$H NMR (300 MHz, CDCl$_3$) δ1.27 (d, J=6.3 Hz, 6H), 4.99 (q, J=6.3 Hz, 1H), 6.42–6.50 (m, 1H), 6.65 (Br s, 1H), 6.92–6.97 (m, 2H).

2.5 M solution of BuLi in cyclohexane (19.7 mL, 49.4 mmol, 3.3 eq.) is added dropwise with stirring to a solution of above N-isopropylcarbamoyl-3,5-difluoroaniline (3.22 g, 14.97 mmol) and TMEDA (10 mL) in THF (25 mL) at −78° C. over 25 min. This resulting mixture is stirred at −78° C. for 20 min, and then ditertbutyldicarbonate (6.8 mL, 29.94 mmol, 2 eq.) is added dropwise with stirring at −78° C. over 10 min. This reaction mixture is stirred at −78° C. for 1 h, and then allowed to warm up to r.t. overnight. Sat. aq. NH$_4$Cl (ca. 50 mL) is added, and the mixture is extracted with excess EtOAc. The combined organic phase is washed with brine and dried over Na$_2$SO$_4$. The solvent is removed under vacuum and the crude product purified by silica gel column chromatography (eluent: 5–10% EtOAc in hexane) to afford the title compound. $^1$H NMR (300 MHz, CDCl3) δ 1.21 (d, J=6 Hz, 6H), 1.57 (s, 9H), 5.00 (q, J=6.3 Hz, 1H), 6.67–6.78 (m, 3H).

Step 2. Preparation of 4-[5-(acetylamino-methyl)-2-oxo-oxazolidin-3-yl]-2,6-difluoro-benzoic Acid Tert-butyl Ester.

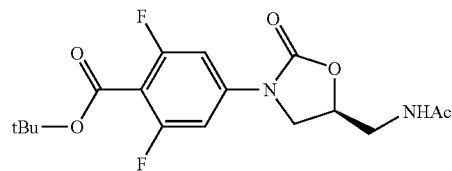

1.0 M t-BuOLi in THF (22.7 mL, 22.71 mmol) is added dropwise with stirring over ca. 5 min to a solution of 2,6-difluoro-4-isopropoxycarbonylamino-benzoic acid tert-butyl ester (2.39 g, 7.57 mmol) in DMF (4.84 mL) and MeOH (0.619 mL, 15.29 mmol) at 0° C. 1-(S)-2-Acetylamino-1-(chloromethyl)ethyl acetate (2.93 g, 15.14 mmol) is added on one portion to the reaction mixture at 0° C. The mixture is allowed to warm up to r.t. and then stirred for another 16 h. Satd. aq. NH$_4$Cl (25 mL) is added, followed by addition of water (25 mL), brine (25 mL) and DCM (50 mL). The organic layer is separated, and aqueous phase is extracted with excess DCM (4×25 mL). The combined organic phase is dried over Na$_2$SO$_4$. The solvent is removed under vacuum. The crude material is purified by silica gel column chromatography (50–100% gradient of EtOAc—hexane) to afford the title compund. $^1$H NMR (300 MHz, CDCl$_3$) δ 2.05 (s, 1H), 3.62–3.67 (m, 2H), 3.72–3.77 (m, 1H), 4.00(t, J=10.2 Hz, 1H) 4.74–4.83 (m, 1H), 6.08–6.13 (Br t, 1H) 7.14 (d, J=12.6 Hz, 2H).

Step 3. Preparation of N-[3-(4-amino-3,5-difluoro-phenyl)-2-oxo-oxazolidin-5-ylmethyl]-acetamide.

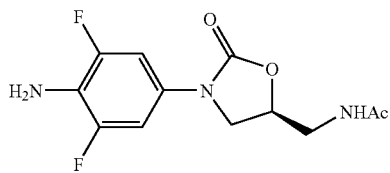

TFA (10 mL) is added with stirring to a solution of 4-[5-(acetylamino-methyl)-2-oxo-oxazolidin-3-yl]-2,6-difluoro-benzoic acid tert-butyl ester (1.44 g, 3.88 mmol) in DCM (20 mL). The resulting solution is stirred for 1 h, and the volatiles removed under vacuum to afford 4-[5-(acetylamino-methyl)-2-oxo-oxazolidin-3-yl]-2,6-difluoro-benzoic acid as a white solid (1.20 g). The acid intermediate is dissolved in dry t-BuOH (15 mL). Diphenylphosphoryl azide (1 mL, 4.65 mmol) and TEA (1.62 mL, 11.64 mmol) are added. The mixture is heated at reflux for 3 h and allowed to cool down to r.t. Solvent is removed under vacuum. The compund, N-[3-(4-tert-butoxycarbonylamino-3,5-difluoro-phenyl)-2-oxo-oxazolidin-5-ylmethyl]-acetamide, is purified by silica gel column chromatography (eluent—EtOAc). The compound is dissolved in DCM (20 mL); and TFA (10 mL) is added. The reaction is stirred at r.t.

for 1 h, and the volatiles are removed under vacuum. The crude aniline is purified by silica gel column chromatography (EtOAc) to afford the pure title compound. MS (m/z): 286 [M+H]+. 1H NMR (300 MHz, CDCl3) δ 2.16 (s, 3H), 3.73–3.74 (m, 2H), 3.90–3.96 (m, 1H), 4.26 (t, J=9.0 Hz, 1H), 4.93–5.01 (m, 1H), 7.32 (d, 8.7 Hz, 2H).

Step 4. Preparation of N-{3-[3,5-difluoro-4-(4-oxo-3,4-dihydro-2H-pyridin-1-yl)-phenyl]-2-oxo-oxazolidin-5-ylmethyl}-acetamide.

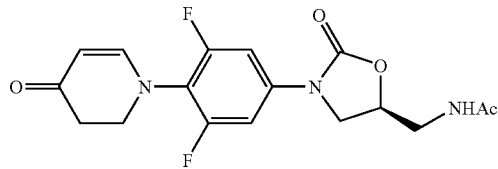

N-[3-(4-Amino-3,5-difluoro-phenyl)-2-oxo-oxazolidin-5-ylmethyl]-acetamide (0.745 g, 2.61 mmol) and hydroxymethylbenzotriazole (0.390 g, 2.61 mmol) are dissolved in dry EtOH (2.0 mL). This resulting solution is refluxed for 5 h, solvent is removed under vacuum, and the resulted aminal intermediate dried under high vacuum. Danishefsky's diene (75.3 mg, 0.43 mmol) is added with stirring to the suspension of above aminal intermediate (0.091 g, 0.21 mmol) in THF (3 mL) at 0° C., followed by trimethylsilyl triflate (ca. 20 mL). The resulting mixture is allowed to warm up to r.t. over 2 h. Sat. aq. NaHCO3 (10 mL) is added, and the mixture extracted with excess EtOAc several times. Solvent is removed under vacuum, and the crude product purified by PTLC (5% MeOH in DCM) followed by RP HPLC (gradient 0–60% of MeCN—water). MS (m/z): 366 [M+H]+. 1H NMR (300 MHz, CDCl3) δ 1.90 (s, 3H), 2.50–2.54 (m, 2H), 3.53–3.64 (m, 2H), 3.84–3.92 (m, 3H), 4.22 (t, 1H, J=9.3 Hz), 4.81–4.89 (m, 1H), 5.04 (d, 1H, J=7.8 Hz), 7.25–7.29 (m, 1H) 7.39–7.51 (m, 3H).

Example 3

Preparation of N-{3-[3-fluoro-4-(4-oxo-3,4-dihydro-2H-pyridin-1-yl)-phenyl]-2-oxo-oxazolidin-5-ylmethyl}-difluoroacetamide Step 1. Preparation of 1-(2-fluoro-4-nitrophenyl)piperidin-4-one

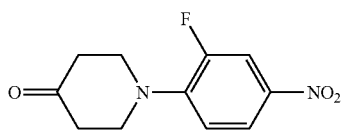

To a stirring solution of 4-piperidone monohydrate hydrochloride (258.7 g, 1.68 mol) and diisopropylethyl amine (590 ml, 3.39 mol) in acetonitrile (2.5 liter) is added 3,4-difluoronitrobenzene (186.3 ml, 1.68 mol). The mixture is heated to 80° C. and stirred overnight. The solvent is cooled to ambient temperature and removed in vacuo. The residue is partitioned between ethyl acetate and 10% aqueous HCl (1.20 liter each). The layers are shaken, the organic layer separated and washed with 10% HCl and brine (800 ml each). The organic layer is dried over MgSO4 and filtered. As the solvent is removed in vacuo a solid began to precipitate out (~¼ volume). The resulting slurry is cooled to 0–5° C. and filtered to afford 333.7 g of the title compound. 1H NMR (400 MHz, CDCl3) δ 2.65 (m, 4 H), 3.65 (m, 4 H), 6.98 (m, 1 H), 7.26 (s, 1 H), 8.00 (m, 1 H); Anal. Calcd for C11H11FN2O3: C, 55.46; H, 4.65; N, 11.76. Found: C, 55.34; H, 4.60; N, 11.69.

Step 2. Preparation of 1-(2-fluoro-4-nitrophenyl)-4-[(trimethylsilyl)oxy]-1,2,3,6-tetrahydropyridine

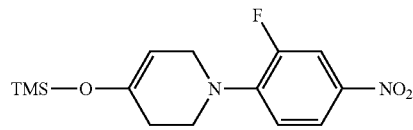

To a stirring solution of the ketone from step 1 (250 g, 1.05 mol) and triethylamine (223 g, 2.20 mol) in toluene (4.2 liter) at 0° C. is added slowly trimethylsilyl trifluoromethanesulfonate (TMS-OTf, 280 g, 1.26 mol) via addition funnel. The stirring is continued for 30 min and the mixture allowed to warm to ambient temperature. Water (5 liter) is added and the aqueous layer extracted with EtOAc (3×500 ml). The organics are combined, dried over MgSO4 and the solvent removed in vacuo. Hexane (4×500 ml) is added and the solvent removed in vacuo. At the fourth co-distillation, a slurry formed (~300 ml). The mixture is cooled to 0° C. and solids filtered. The filtrated is concentrated to a slurry, cooled and filtered (2nd crop). Solids are combined to result in 273.7 g (84%) title compound as a yellow solid. 1H NMR (CDCl3) δ 0.21 (s, 9 H), 2.20 (brs, 2 H), 3.52 (brs, 2 H), 3.62 (brs, 2 H), 4.89 (brs, 1 H), 6.65 (t, J=8 Hz, 1 H), 7.67 (d, J=12 Hz, 1 H), 7.73 (d, J=12 Hz, 1 H. Anal. Calcd for C14H19FN2O3Si: C, 54.17; H, 6.17; N, 9.02. Found: C, 54.01; H, 6.29; N, 9.15.

Step 3. Preparation of 1-(2-Fluoro-4-nitro-phenyl)-2,3-dihydro-1H-pyridin-4-one.

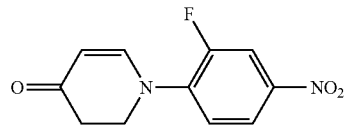

To a stirring solution of the enol silyl ether from step 2 (100.0 g, 322 mmol) and allyl methyl carbonate (43.6 g, 386 mmol) in DMSO (625 ml) at ambient temperature is added Pd(OAc)2 (7.20 g, 32 mmol). The resulting solution is stirred under N2 at ambient temperature overnight. H2O (1 liter) is added and solvent allowed to cool to ambient temperature. The aqueous layer is extracted with EtOAc (2×800 ml) and the organic layers combined, washed with brine (800 ml) and organics dried over MgSO4. The solvent is removed and residue recrystallized from EtOAc/MTBE to afford 53.6 g (70%) of the title compound as a yellow solid. 1H NMR (CDCl3) δ 2.71 (m, 2 H), 4.06 (m, 2 H), 5.41 (d, J=8 Hz, 1 H), 7.25 (m, 1 H), 7.35 (d, J=8 Hz, 1 H), 8.08 (m, 2 H); Anal. Calcd for C11H9FN2O3: C, 55.94; H, 3.84; N, 11.86; F, 8.04. Found: C, 55.82; H, 3.81; N, 11.67.

Step 4. Preparation of 1-(4-Amino-2-fluoro-phenyl)-2,3-dihydro-1H-pyridin-4-one.

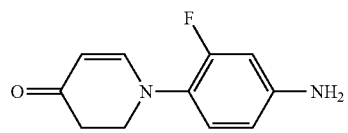

In a 500 ml Parr bottle, the nitrophenyl compound from step 3 (35 g, 148.3 mmol), Pd/CaCO$_3$ (3.5 g, 10 wt %) and acetic acid (17 ml, 297 mmol) are combined in THF (350 ml). The mixture is hydrogenated at 40° C. under 15 psi hydrogen for 6 h at which time the reaction is complete by HPLC. The reaction mixture is filtered through a GF/F filter and the catalyst cake washed with THF (350 ml). The filtrate is partitioned between 500 ml of NaHCO$_3$ and 500 ml of ethyl acetate. The organic layer is washed again with 500 ml of NaHCO$_3$. The organic layer is separated and dried over MgSO$_4$. The mixture is filtered, and the filtrated is concentrated in vacuo to afford 29.0 g (95% recovery) of crude title compound. MS (ESI–) for C$_{11}$H$_{11}$FN$_2$O m/z 205.0 (M–H)$^-$; $^1$H NMR (MeOD) δ 7.37 (d, J=7.5, 1 H), 7.02 (t, J=9.0, 1 H), 6.47 (m, 3 H), 5.07 (d, J=7.4, 1 H), 3.84 (t, J=7.8, 2 H), 2.58 (t, J=7.8, 1 H); $^{13}$C NMR (MeOD) δ 195.1, 160.1, 157.7, 157.1, 151.2, 127.9, 124.0, 122.9, 112.2, 103.5, 103.2, 100.2, 51.4, 36.8.

Step 5. Preparation of isobutyl 3-fluoro-4-(4-oxo-3,4-dihydropyridin-1(2H)-yl)phenylcarbamate.

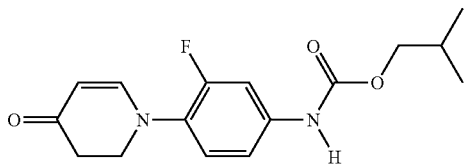

To a cold (0° C.) stirring solution of the aniline from step 4 (62.0 g, 300.7 mmol) and pyridine (29.1 ml, 360.8 mmol) in dichloromethane (1095 ml) is added isobutyl chloroformate (42.9 ml, 330.7 mmol), and the mixture is stirred at ambient temperature for 90 min. Upon completion of the reaction the solvent is removed in vacuo, and the residual material is redissolved in dichloromethane (800 ml) and ethyl acetate (1100 ml). The mixture is washed with 10% aqueous HCl (1100 ml), and aqueous layer is extracted with 1:9/dichloromethane:ethyl acetate (1100 ml). The organic layers are combined and washed with brine (1100 ml). The organic layer is dried over MgSO$_4$ and filtered. The filtrate is concentrated in vacuo. The residual material is recrystallized in 1:9/dichloromethane:ethyl acetate to afford 66.9 g (72% yield) of the title compound as a brown solid. $^1$H NMR (400 MHz, DMSO-d$_6$) δ 0.93 (d, 6 H), 1.93 (m, 1 H), 2.47 (m, 2 H), 3.84 (m, 2 H), 3.89 (m, 2 H), 4.96 (d, 1 H) 7.29 (m, 2 H), 7.48 (m, 2 H), 9.92 (brs, 1 H).

Step 6. Preparation of tert-butyl {(5S)-3-[3-fluoro-4-(4-oxo-3,4-dihydropyridin-1(2H)-yl)phenyl]-2-oxo-1,3-oxazolidin-5-yl}methylcarbamate.

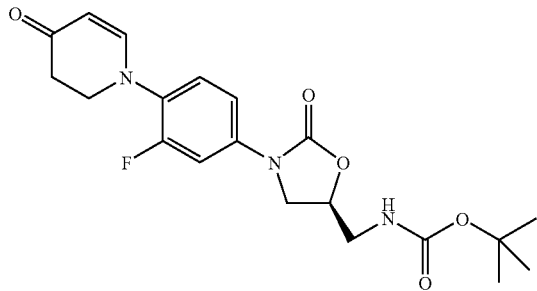

Solid LiOBu$^t$ is added portionwise to a stirring mixture of the carbamate from Step 5 (80 g, 261 mmol) and PNU-277117 (109.6 g, 522 mmol) in CH$_3$CN/THF (3:2 v/v 400 ml) at 0° C. under N$_2$. The cooling is removed and mixture is stirred overnight at ambient temperature. The mixture is quenched by the addition of saturated aqueous NH$_4$Cl (320 ml). The mixture is partitioned between EtOAc (800 ml) and H$_2$O (1600 ml). The layers are shaken and the organic layer separated, dried over MgSO$_4$ and solvent removed in vacuo. The residue is purified by SiO2 flash column chromatography (eluant 3% MeOH/CH$_2$Cl$_2$) to afford 73.7 g (70%) title compound as a brown solid. $^1$H NMR (CDCl$_3$) δ 1.40 (s, 9 H), 2.65 (t, J=8 Hz, 2 H), 3.54 (m, 2 H), 3.87 (m, 1 H), 3.92 (t, J=8 Hz, 2 H), 4.03 (t, J=8 Hz, 1 H), 4.78 (brs, 1 H), 5.01 (brs, 1 H), 5.22 (d, J=8 Hz, 1 H), 7.14 (m, 1 H), 7.21 (m, 1 H), 7.57 (d, 1 H);

Step 7. Preparation of 1-{4-[(5 S)-5-(aminomethyl)-2-oxo-1,3-oxazolidin-3-yl]-2-fluorophenyl}-2,3-dihydropyridin-4 (1H)-one Hydrochloride.

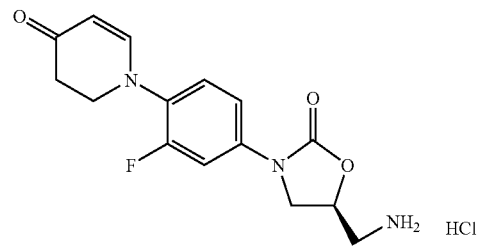

4.0 M HCl in 1,4-dioxane (25 mL) is added to {3-[3-fluoro-4-(4-oxo-3,4-dihydro-2H-pyridin-1-yl)-phenyl]-2-oxo-oxazolidin-5-ylmethyl}-carbamic acid tert-butyl ester (1.05 g, 2.6 mmol), and the mixture is stirred at r.t. for 45 min. The solvent is removed under vacuum. Resulted residue is dissolved in excess MeOH and then evaporated again under vacuum to afford 1-[4-(5-aminomethyl-2-oxo-oxazolidin-3-yl)-2-fluoro-phenyl]-2,3-dihydro-1H-pyridin-4-one hydrochloride as hydroscopic orange crystals. Yield 0.8 g (quant). MS (m/z): 306 [M+H]$^+$.

Step 8. Preparation of N-{3-[3-fluoro-4-(4-oxo-3,4-dihydro-2H-pyridin-1-yl)-phenyl]-2-oxo-oxazolidin-5-ylmethyl}-difluoroacetamide.

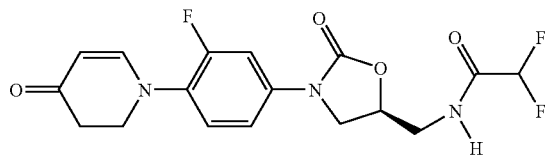

Difluoroacetic acid (0.031 mL, 0.48 mmol) is added to a solution of 1-[4-(5-aminomethyl-2-oxo-oxazolidin-3-yl)-2-fluoro-phenyl]-2,3-dihydro-1H-pyridin-4-one hydrochloride (0.150 g, 0.44 mmol) in DMF (1.5 mL) with pyridine (0.071 mL, 0.88 mmol), followed by addition of diisopropylcarbodiimide (0.076 mL, 0.48 mmol). The mixture is stirred at r.t. for 1 h. Most of the solvent is removed under high vacuum, and the product is purified by silica gel column chromatography (eluent: 2% MeOH in DCM). The chromatography is repeated (eluent: 1% MeOH in DCM) to afford N-{3-[3-Fluoro-4-(4-oxo-3,4-dihydro-2H-pyridin-1-yl)-phenyl]-2-oxo-oxazolidin-5-ylmethyl} difluoroacetamide as a white solid. Yield 0.065 g (39%). MS (m/z): 384 [M+H]$^+$. $^1$H NMR (300 MHz, DMSO-d$_6$) δ 9.36 (t, J=5.5 Hz, 1H), 7.82–7.49 (m, 4H), 6.44 (t, J=53.6 Hz, 1H), 5.18 (d, J=7.7 Hz, 1H), 5.03–4.98 (m, 1H), 4.38–4.32 (m, 1H), 4.07 (t, J=7.4 Hz, 2H), 3.97 (dd, J=6.3 and 9.3 Hz, 1H), 3.72 (t, J=5.5 Hz, 1H), 3.51–3.49 (m, 2H), 2.69–2.64 (m, 2H).

Example 4

Preparation of N-{3-[3-fluoro-4-(4-oxo-3,4-dihydro-2H-pyridin-1-yl)-phenyl]-2-oxo-oxazolidin-5-ylmethyl}-propionamide

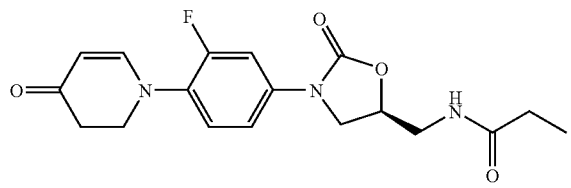

Propionic anhydride (104 mg, 0.8 mmol) is added to a solution of the amine hydrochloride from Step 7 of Example 3 (160 mg, 0.39 mmol) and pyridine (0.128 mL, 1.6 mmol) in DCM (4 mL) and DMF (1 mL). After 48 h the reaction is concentrated under reduced pressure and the crude title compound is purified by silica gel column chromatography (gradient: 10% MeOH in EtOAc) followed by recrystallization from MeOH. MS (m/z): 362 [M+1]$^+$. $^1$H NMR (300 MHz, DMSO-d$_6$) δ 8.14 (Br t, 1H), 7.60 (dd, J=11.81 Hz, 2.2 Hz, 1H), 7.48–7.29 (m, 3H), 4.98 (d, J=7.7 Hz, 1H), 4.75–4.71 (m, 1H), 4.11 (t, J=7.7 Hz, 1H), 3.76–3.71 (m, 1H), 3.43–3.39 (m, 2H), 3.29 (d, J=7.1 Hz, 2H), 2.49–2.44 (m, 2H), 2.08 (q, J=7.4 Hz, 2H), 0.94 (t, J=7.4 Hz, 3H).

Example 5

Preparation of 2,2-dichloro-N-{3-[3-fluoro-4-(4-oxo-3,4-dihydro-2H-pyridin-1-yl)-phenyl]-2-oxo-oxazolidin-5-ylmethyl}-acetamide

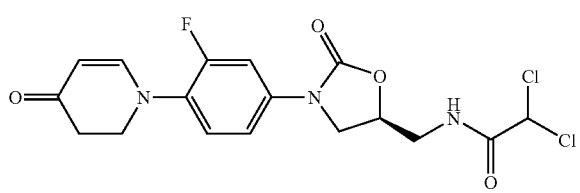

TFA (0.75 mL) is added to a solution of the carbamate from Step 6 of Example 3 (100 mg, 0.247 mmol) in dichloroethane (3.0 mL). This solution is stirred for 1.5 h., and the solvent is removed under vacuum. The residue is dissolved in MeOH (4.0 mL). TEA (105 mg, 1 mmol) is added to the mixture, followed by adding ethyl dichloroacetate (77 mg, 0.49 mmol). The mixture is stirred at r.t. for 16 h. Solvent is removed under vacuum, and the crude product purified by silica gel column chromatography (gradient 1% to 2% MeOH in DCM). MS (m/z): 417 [M+1]$^+$. $^1$H NMR (300 MHz, DMSO-d$_6$) δ 9.17 (t, J=5.5 Hz, 1H), 7.79 (d, J=14.3 Hz, 1H), 7.69–7.48 (m, 3 H), 6.67 (s, 1H), 5.17 (d, J=7.7 Hz, 1H), 5.05–4.99 (m, 1H), 4.35 (t, J=9.1 Hz, 1H), 4.06 (t, J=7.7 Hz, 3H), 3.93 (dd, J=6.0 and 9.3 Hz, 1H), 3.74–3.72 (m, 2H), 3.51–3.49 (m, 2H).

Example 6

Preparation of 2,2-difluoro-N-{3-[3-fluoro-4-(4-oxo-3,4-dihydro-2H-pyridin-1-yl)-phenyl]-2-oxo-oxazolidin-5-ylmethyl}-thioacetamide Step 1. Preparation of Sifluoro-acetic Acid-O-(3,3-diphenyl-propyl) Ester.

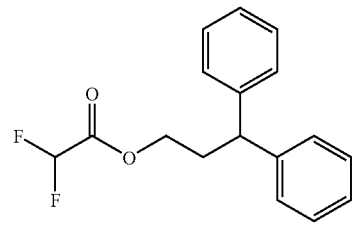

Dicyclohexylcarbodiimide (12.6 g, 62.4 mmol) is added portion wise with stirring to a solution of difluoroacetic acid (4.0 g, 4.0 mL, 62.4 mmol), 3,3-diphenyl-1-propanol (14.4 g, 13.8 mL, 68.4 mol) and 4-dimethylaminopyridine (732 mg, 6.2 mmol) in ethyl ether (180 mL) at 0–5° C. The reaction mixture is allowed to warm up to r.t., and stirred at r.t. overnight. Precipitated urea by-product is filtered off and washed with excesses of ethyl ether. Combined filtrates are removed under vacuum, and the title compound is purified by silica gel flash chromatography (eluent: 5% ethyl ether in hexanes). White crystalline solid (17.3 g, 96%). HPLC R$_t$=7.2. MS (m/z): 291 [M+H]$^+$.

Step 2. Preparation of Sifluoro-thioacetic Acid-O-(3,3-diphenyl-propyl) Ester.

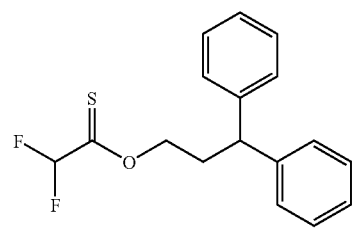

A solution of difluoro-acetic acid-O-(3,3-diphenyl-propyl)ester (17.3 g, 59.7 mmol) in xylene (100 mL) is treated with Lawesson's reagent (29.0 g, 71.6 mmol). The reaction mixture is stirred at 135–145° C. for 24 h. Resulted solids are filtered off and washed with excess of ethyl acetate. Remove the solvent under vacuum, and the title compound is purified by silica gel flash chromatography (eluent: hexanes). HPLC R$_t$=7.6. MS (m/z): 307 [M+H]$^+$.

Step 3. Preparation of 2,2-Difluoro-N-{3-[3-fluoro-4-(4-oxo-3,4-dihydro-2H-pyridin-1-yl)-phenyl]-2-oxo-oxazolidin-5-ylmethyl}-thioacetamide.

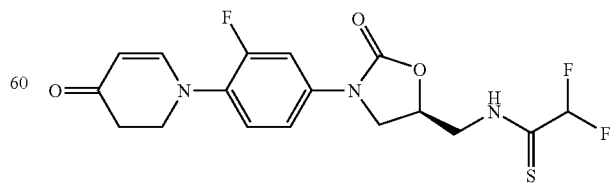

Difluoro-thioacetic acid-O-(3,3-diphenyl-propyl)ester (84 mg, 0.25 mmol) is added to a solution of 1-[4-(5-aminomethyl-2-oxo-oxazolidin-3-yl)-2-fluoro-phenyl]-2,3-dihydro-1H-pyridin-4-one in MeCN (1.2 mL) and DMF (0.2 mL). This solution is stirred for 36 h at which time the reaction is concentrated under reduced pressure and the title compound is purified by silica gel column chromatography (eluent: 1% MeOH in EtOAc). Yield 45 mg (41%). MS (m/z) 400 [M+1]$^+$. $^1$H NMR (300 MHz, DMSO-d$_6$) δ 11.32 (s, 1H), 7.83–7.51 (m, 4H), 6.69 (t, J=55.2 Hz, 1H), 5.25–5.17 (m, 2H), 4.39 (t, J=9.1 Hz,1H), 4.22–4.03 (m, 6H), 3.55–3.49 (m, 2H).

Example 7

Preparation of {3-[3-fluoro-4-(4-oxo-3,4-dihydro-2H-pyridin-1-yl)-phenyl]-2-oxo-oxazolidin-5-ylmethyl}-carbamic Acid Methyl Ester

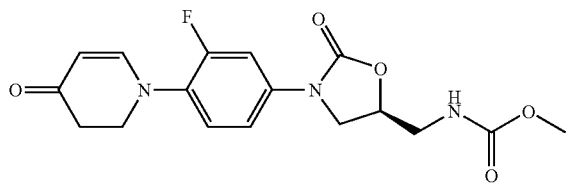

TFA (1.5 mL) is added to a solution of {3-[3-fluoro-4-(4-oxo-3,4-dihydro-2H-pyridin-1-yl)-phenyl]-2-oxo-oxazolidin-5-ylmethyl}-carbamic acid tert-butyl ester (300 mg, 0.74 mmol) in dichloroethane (6.0 mL). This solution is stirred for 1.5 h. Removed solvent under vacuum, and the residue is dissolved in MeCN (3.0 mL). TEA (0.41 mL, 3 mmol) is added followed by methyl chloroformate (98 mg, 1 mmol). The mixture is stirred at r.t. for 16 h. Solvent is removed under vacuum, and the residue is purified by silica gel column chromatography (eluent: EtOAc) to afford the product as a yellow solid. Yield 100 mg (37%). MS (m/z): 364 [M+1]$^+$. $^1$H NMR (300 MHz, DMSO-d$_6$) δ7.62–7.30 (m, 4H), 4.98 (dd, J=7.7 Hz, 3.0 Hz, 1H), 4.80–4.65 (m, 1H), 4.11 (dd, J=6.86 Hz, 2H), 3.79–3.74 (m, 1H), 3.53 (s, 3H), 3.40–3.30 (m, 2H), 2.49–2.44 (m, 2H).

Example 8

Preparation of 2,2-dichloro-N-{2-oxo-3-[4-(4-oxo-3,4-dihydro-2H-pyridin-1-yl)-phenyl]-oxazolidin-5-ylmethyl}-acetamide

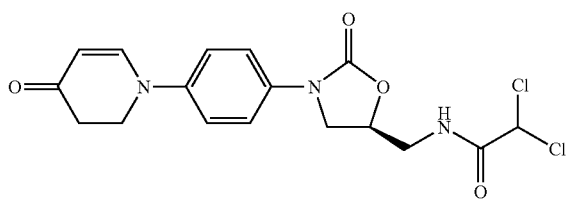

Step 1. Preparation of 1-(4-nitro-phenyl)-piperidin-4-one.

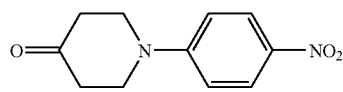

1-(4-Nitro-phenyl)-piperidin-4-one is prepared following the method described in Example 3 using 4-nitrobenzene (9.5 g, 67.3 mmol) as the starting agent. The reaction is performed at 50° C. overnight. MS (m/z): 221 [M+1]$^+$. $^1$H NMR (300 MHz, CDCl$_3$)δ8.15 (d, J=9.3 Hz, 2H), 6.83 (d, J=9.6 Hz, 2H), 3.80 (t, J=7.7 Hz 4H), 2.61 (t, J=6.6 Hz, 4H).

Step 2. Preparation of 1-(4-nitro-phenyl)-4-(triisopropyl-silanyloxy)-1,2,3,6-tetrahydro-pyridine.

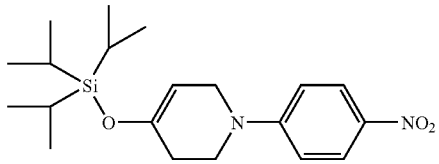

1-(4-Nitro-phenyl)-4-(triisopropyl-silanyloxy)-1,2,3,6-tetrahydro-pyridine is prepared from 1-(4-nitro-phenyl)-piperidin-4-one (9.90 g, 45 mmol) following the method described for Example 3 and purified by silca gel flash column chromatography (gradient 0 to 15% EtOAc in hexanes). Yield 9.70 g (57%). MS (m/z): 377 [M+1]$^+$. $^1$H NMR (300 MHz, DMSO) δ8.04 (d, J=9.3 Hz, 2H), 4.92 (d, J=9.6, 2H), 4.92 (t, J=3.0 Hz, 1H), 3.88 (br. d, 2H), 3.66 (t, J=5.8 Hz, 2H), 2.50–2.20 (m, 2H), 1.97–1.12 (m, 3H), 1.02 (d, J=6.6 Hz, 18H).

Step 3. Preparation of 1-(4-nitro-phenyl)-2,3-dihydro-1H-pyridin-4-one.

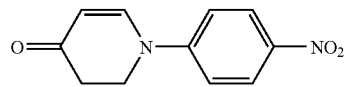

1-(4-Nitro-phenyl)-2,3-dihydro-1H-pyridin-4-one is prepared from 1-(4-nitro-phenyl)-4-(triisopropyl-silanyloxy)-1, 2,3,6-tetrahydro-pyridine (2.50 g, 6.65 mmol) following the method described for Example 3. The reaction is performed for 4 h, and the product purified by silca gel flash column chromatography (gradient 5% to 60% EtOAc in hexanes). Yield 2.10 g (57%). MS (m/z): 219 [M+1]$^+$. $^1$H NMR (300 MHz, CDCl,) δ8.39 (d, J=9.1 Hz, 2H), 7.49 (d, J=8.0 Hz, 1H), 7.14 (d, J=9.1 Hz, 2H), 5.39 (d, J=8.0 Hz, 1H), 4.06 (t, J=7.4 Hz, 4H), 2.72 (t, J=7.4 Hz, 4H).

Step 4. Preparation of 1-(4-aminophenyl)-2,3-dihydro-1H-pyridin-4-one.

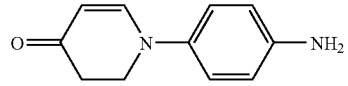

1-(4-Aminophenyl)-2,3-dihydro-1H-pyridin-4-one is prepared from 1-(4-nitro-phenyl)-2,3-dihydro-1H-pyridin-4-one (2.75 g, 12.6 mmol) following the method described for Example 3. MS (m/z): 211 (M+Na)$^+$.

Step 5. Preparation of [4-(4-oxo-3,4-dihydro-2H-pyridin-1-yl)-phenyl]-carbamic Acid Benzyl Ester.

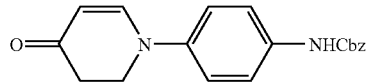

[4-(4-Oxo-3,4-dihydro-2H-pyridin-1-yl)-phenyl]-carbamic acid benzyl ester is prepared from 1-(4-aminophenyl)-2,3-dihydro-1H-pyridin-4-one (2.0 g, 10.6 mmol) following the method described for Example 3 and purified by silca gel flash column chromatography (gradient 20% to 100% EtOAc in hexanes). MS (m/z): 323 [M+1]+. 1H NMR (300 MHz, DMSO-d6) δ 9.97 (br. s, 1H), 7.87 (d, J=7.7 Hz, 2H), 7.67–7.51 (m, 6H), 7.38 (d, J=9.1 Hz, 2H), 5.33 (s, 2H), 5.14 (d, J=7.7 Hz, 1H), 4.11 (t, J=7.4 Hz, 2H), 2.65 (t, J=7.4 Hz, 2H).

Step 6. Preparation of {3-[4-(4-oxo-3,4-dihydro-2H-pyridin-1-yl)-phenyl]-2-oxo-oxazolidin-5-ylmethyl}-carbamic Acid Tert-butyl Ester.

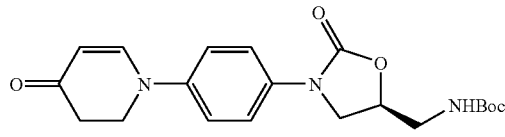

{3-[4-(4-Oxo-3,4-dihydro-2H-pyridin-1-yl)-phenyl]-2-oxo-oxazolidin-5-ylmethyl}-carbamic acid tert-butyl ester is prepared from [4-(4-oxo-3,4-dihydro-2H-pyridin-1-yl)-phenyl]-carbamic acid benzyl ester (1.8 g, 5.60 mmol) following the method described in example 3 and purified by silca gel flash column chromatography to give the title compound (gradient 40% to 100% EtOAc in hexanes). MS (m/z): 388 [M+1]+. 1H NMR (300 MHz, DMSO-d6) δ7.93 (d, J=7.7 Hz, 1H), 7.73 (d, J=9 Hz, 2H), 7.50–7.40 (m, 3H), 5.17 (d, J=7.7 Hz, 1H), 4.89–4.85 (m, 1H), 4.33–4.12 (m, 3H), 4.00–3.95 (m, 1H), 3.50–3.45 (m, 2H), 2.68–2.1 (m, 2H), 1.55 (s, 9H).

Step 7. Preparation of 1-[4-(5-aminomethyl-2-oxo-oxazolidin-3-yl)-phenyl]-2,3-dihydro-1H-pyridin-4-one Hydrochloride.

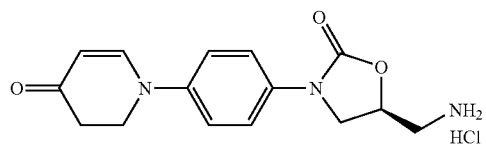

1-[4-(5-Aminomethyl-2-oxo-oxazolidin-3-yl)-phenyl]-2,3-dihydro-1H-pyridin-4-one hydrochloride is prepared from {3-[4-(4-oxo-3,4-dihydro-2H-pyridin-1-yl)-phenyl]-2-oxo-oxazolidin-5-ylmethyl}-carbamic acid tert-butyl ester following the method described for Example 3 using 25% TFA in DCE. MS (m/z): 288 [M−HCl+H]+.

Step 8. Preparation of 2,2-dichloro-N-{2-oxo-3-[4-(4-oxo-3,4-dihydro-2H-pyridin-1-yl)-phenyl]-oxazolidin-5-ylmethyl}-acetamide.

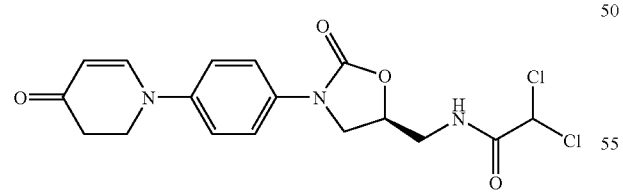

2,2-Dichloro-N-{2-oxo-3-[4-(4-oxo-3,4-dihydro-2H-pyridin-1-yl)-phenyl]-oxazolidin-5-ylmethyl}-acetamide is prepared from {3-[4-(4-oxo-3,4-dihydro-2H-pyridin-1-yl)-phenyl]-2-oxo-oxazolidin-5-ylmethyl}-carbamic acid tert-butyl ester (100 mg, 0.25 mmol) following the method described for Example 5. Purification is accomplished by silica gel chromatography (eluent 2% MeOH in EtOAc). MS (m/z): 382 [M+1]. 1H NMR (300 MHz, DMSO-d6) δ8.98 (t, J=5.2 Hz, 1H), 7.72 (d, J=7.7 Hz, 1H), 7.53 (d, J=9.1 Hz, 2H), 7.27 (d, J=9.1 Hz, 2H), 6.48 (s, 1H), 4.97 (d, J=7.7 Hz, 2H), 4.81–4.76 (m, 1H), 4.14 (t, J=9.1, 1H), 3.95 (t, J=7.4 Hz, 2H), 3.72 (dd, J=6.6 and 9.1 Hz, 1H), 3.57–3.51 (m, 2H), 3.31–2.45 (m, 2H).

Example 9

Preparatioin of N-{2-oxo-3-[4-(4-oxo-3,4-dihydro-2H-pyridin-1-yl)-phenyl]-oxazolidin-5-ylmethyl}-acetamide

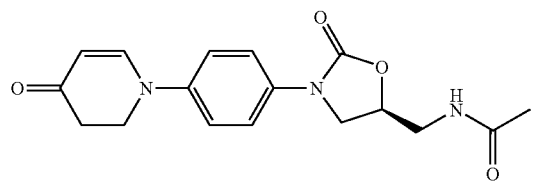

1.0 M LiOBu-t in THF (5 mL, 5 mmol) is added dropwise with stirring to a solution of acetic acid 1-(acetylaminomethyl)-2-chloro-ethyl ester (0.600 g, 3.10 mmol) in DMF (1 mL) and MeOH (0.127 mL) under nitrogen atmosphere at 0° C. [4-(4-Oxo-3,4-dihydro-2H-pyridin-1-yl)-phenyl]-carbamic acid benzyl ester (0.500 g, 1.55 mmol; prepared as described for Example 8), is added, and the mixture is allowed to gradually warm up to r.t. and stirred for additional 24 h. The mixture is quenched with saturated aq. NH4Cl (20 mL), diluted with aq. NaCl, and extracted with EtOAc (3×). The organic layers are combined and washed with brine, and dried over MgSO4. The solvent is removed under vacuum, and the crude product purified by silica gel flash chromatography (gradient 20% to 100% EtOAc—hexanes) to afford the title compound as a white solid. Yield 137 mg (26%). MS (m/z): 330 [M+H]+. 1H NMR (300 MHz, DMSO-d6) δ 8.24 (br. t, J=5.8 Hz, 1H), 7.72 (d, J=7.7, 1H), 7.53 (d, J=9.1, 2H), 7.27 (d, J=9.1, 2H), 4.97 (d, J=7.7 Hz, 1H), 4.72–4.67 (m, 1H), 4.10 (t, J=9.1 Hz, 2H), 3.75–3.69 (m, 1H), 3.40 (t, J=5.5 Hz, 2H), 2.50–2.49 (m, 2H), 1.82 (s, 3H).

Example 10

Preparation of 2,2-difluoro-N-{2-oxo-3-[4-(4-oxo-3,4-dihydro-2H-pyridin-1-yl)-phenyl]-oxazolidin-5-ylmethyl}-thioacetamide

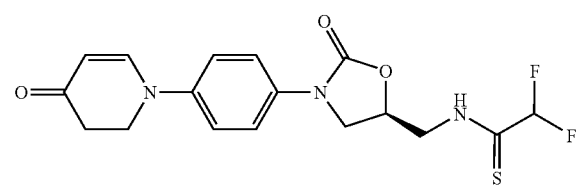

TFA (1 mL) is added to a solution of {3-[4-(4-oxo-3,4-dihydro-2H-pyridin-1-yl)-phenyl]-2-oxo-oxazolidin-5-ylmethyl}-carbamic acid tert-butyl ester (200 mg, 0.52 mmol) in DCE (4 mL). This solution is stirred for 1.5 h, and the mixture is concentrated under vacuum to afford TFA salt of 1-[4-(5-Aminomethyl-2-oxo-oxazolidin-3-yl)-2-fluoro-phenyl]-2,3-dihydro-1H-pyridin-4-one. TEA (105 mg, 1.04 mmol) is added to a solution of the above salt in MeOH (4.0 mL) followed by difluorothioacetic acid-O-(3,3-diphenyl-propyl)ester (84 mg, 0.25 mmol). The mixture is stirred for 4 h at 50° C., and the solvent is removed under vacuum. The crude product is purified by silica gel column chromatography (eluent: 1.5% MeOH in EtOAc). MS (m/z): 382 [M+1]+. 1H NMR (300 MHz, DMSO-d6) δ7.93 (d, J=7.7 Hz, 1H), 7.73 (d, J=9.3 Hz, 2H), 7.49 (d, J=9.3 Hz, 2H), 6.69 (t, J=55.2 Hz, 1H), 5.21–5.17 (m, 2H), 4.38 (t, J=9.1 Hz, 1H), 4.18–4.12 (m, 4H), 4.05 (dd, J=6.3 and 9.1 Hz, 1H), 3.48 (d, J=7.1 Hz, 2H).

Example 11

Preparation of 2,2-difluoro-N-{2-oxo-3-[4-(4-oxo-3,4-dihydro-2H-pyridin-1-yl)-phenyl]-oxazolidin-5-ylmethyl}-acetamide

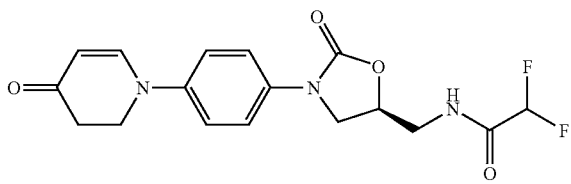

The compound is prepared from {3-[4-(4-oxo-3,4-dihydro-2H-pyridin-1-yl)-phenyl]-2-oxo-oxazolidin-5-ylmethyl}-carbamic acid tert-butyl ester (250 mg, 0.64 mmol) and ethyl difluoroacetate (120 mg, 0.96 mmol) following the method described for Example 5 (using ethyl difluoroacetate as starting agent). The product is purified by silica gel column chromatography (eluent 1% MeOH in EtOAc) and recrystallized from MeOH to provide the title compound. MS (m/z): 366 [M+1]. 1H NMR (300 MHz, DMSO) δ 9.16 (t, J=5.8 Hz, 1H), 7.73 (d, J=8.0 Hz, 1H), 7.53 (d, J=9.1 Hz, 2H), 7.28 (d, J=9.1 Hz, 2H), 6.24 (t, J=53.0 Hz, 1H), 4.98 (d, J=7.7 Hz, 1H), 4.80–4.75 (m, 1H), 4.14 (t, J=9.1 Hz, 1H), 3.97–3.92 (m, 2H), 3.76 (dd, J=6.3 and 9.1 Hz, 1H), 3.52 (t, J=5.5 Hz, 2H), 2.47 (t, J=7.1 Hz, 2H).

Example 12

Preparation of N-{2-oxo-3-[4-(4-oxo-3,4-dihydro-2H-pyridin-1-yl)-phenyl]-oxazolidin-5-ylmethyl}-propionamide

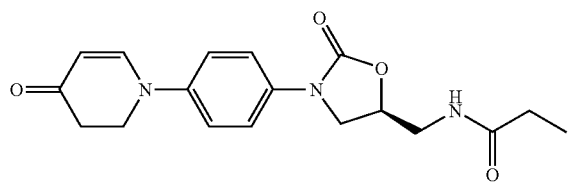

The compound is prepared from {3-[4-(4-oxo-3,4-dihydro-2H-pyridin-1-yl)-phenyl]-2-oxo-oxazolidin-5-ylmethyl}-carbamic acid tert-butyl ester (232 mg, 0.60 mmol) and propionic anhydride (120 mg, 0.96 mmol) following the method described for Example 5. The crude product is purified by silica gel column chromatography (2% to 5% MeOH in EtOAc) to give the title compound as solid. MS (m/z): 344 [M+1]+. 1H NMR (300 MHz, DMSO-d6) δ8.16 (br. t, 1H), 7.72 (d, J=8.0 Hz, 1H), 7.52 (d, J=7.1 Hz, 2H), 7.27 (d, J=7.4 Hz, 2H), 4.97 (d, J=7.4 Hz, 1H), 4.80–4.65 (m, 1H), 4.10 (t, J=7.7 Hz, 2H), 3.94 (d, J=6.9 Hz, 2H), 3.41–3.99 (m, 2H), 2.49–2.47 (m, 2H), 2.09 (q, J=5.8 Hz, 2H), 0.93 (t, J=7.4 Hz, 3H).

Example 13

Preparation of N-{3-[3,5-difluoro-4-(4-oxo-3,4-dihydro-2H-pyridin-1-yl)-phenyl]-2-oxo-oxazolidin-5-ylmethyl}-2,2-difluoro-acetamide Step 1. Preparation of 1-(2,6-difluoro-4-nitro-phenyl)-piperidin-4-one.

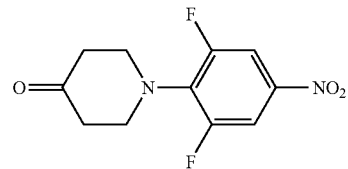

The title compound is prepared following the method described for Example 3 using 1,2,6-trifluoro-4-nitrobenzene as starting agent (3.00 g, 16.94 mmol). MS (m/z): 257 [M+1]+. 1H NMR (300 MHz, CDCl3) δ7.80 (d, J=9.6 Hz, 1H), 3.63 (dd, J=6.0 and 6.2 Hz, 4H), 2.59 (dd, J=6.0 and 6.0 Hz, 4H).

Step 2. Preparation of 1-(2,6-difluoro-4-nitro-phenyl)-4-(triisopropyl-silanyloxy)-1,2,3,6-tetrahydro-pyridine.

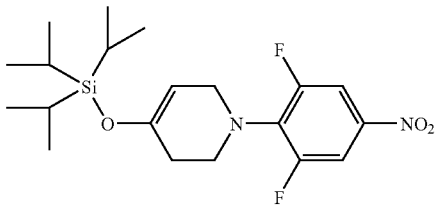

The title compound is prepared from 1-(2,6-difluoro-4-nitro-phenyl)-piperidin-4-one (1.73 g, 6.75 mmol) following the method described for Example 3 and purified by silca gel flash chromatography (gradient 0 to 25% EtOAc in hexanes). 1H NMR (300 MHz, CDCl3) δ7.73 (d, J=10.4 Hz, 2H), 4.89–4.86 (m, 1H), 3.90–3.87 (m, 2H), 3.50–3.45 (m, 2H), 2.34–2.30 (m, 2H), 1.07–0.99 (m, 21H).

Step 3. 1-(2,6-difluoro-4-nitro-phenyl)-2,3-dihydro-1H-pyridin-4-one.

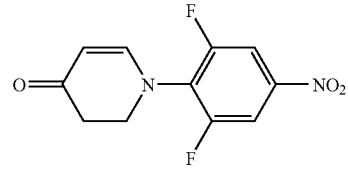

The title compound is prepared from 1-(2,6-difluoro-4-nitro-phenyl)-4-(triisopropyl-silanyloxy)-1,2,3,6-tetrahydro-pyridine (3.10 g, 7.51 mmol) following the method described in example 3 and purified by silca gel flash chromatography (eluent: 50% EtOAc in hexanes). MS (m/z): 255 [M+1]+. 1H NMR (300 MHz, CDCl3) δ8.23 (d, J=8.8 Hz, 2H), 7.53–7.49 (m, 1H), 5.23 (d, J=8.0 Hz, 1H), 3.95 (t, J=6.9 Hz, 2H), 2.53–2.47 (m, 2H).

Step 4. Preparation of 1-(4-amino-2,6-fluoro-phenyl)-2,3-dihydro-1H-pyridin-4-one.

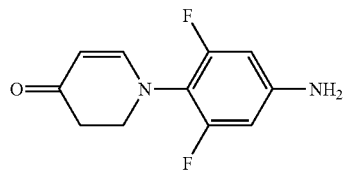

The title compound is prepared from 1-(2,6-difluoro-4-nitro-phenyl)-2,3-dihydro-1H-pyridin-4-one (1.34 g, 5.27 mmol) following the method described for Example 3.

Step 5. Preparation of [3,5-difluoro-4-(4-oxo-3,4-dihydro-2H-pyridin-1-yl)-phenyl]-carbamic Acid Benzyl Ester.

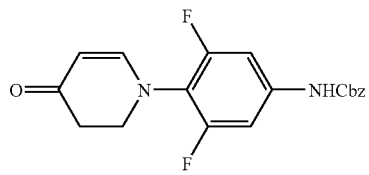

The title compound is prepared from 1-(4-amino-2,6-difluorophenyl)-2,3-dihydro-1H-pyridin-4-one (1.08 g, 4.81 mmol) following the method described in Example 3 and purified by silca gel flash chromatography (gradient: 25% to 75% EtOAc in hexanes). MS (m/z): 359 [M+1]$^+$. $^1$H NMR (300 MHz, CDCl$_3$) δ7.39–7.35 (m, 5H), 7.13–6.91 (m, 5H), 5.20–5.17 (m, 3H), 3.79 (t, J=7.1 Hz, 4H), 2.62 (m, J=7.69 Hz, 4H).

Step 6. Preparation of {3-[3,5-difluoro-4-(4-oxo-3,4-dihydro-2H-pyridin-1-yl)-phenyl]-2-oxo-oxazolidin-5-ylmethyl}-carbamic Acid Tert-butyl Ester.

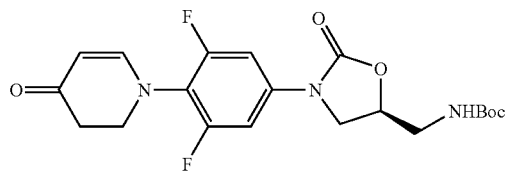

The title compound is prepared from [3,5-difluoro-4-(4-oxo-3,4-dihydro-2H-pyridin-1-yl)-phenyl]-carbamic acid benzyl ester (1.50 g, 4.18 mmol) following the method described in Example 3 and purified by silca gel flash chromatography (gradient 50% to 100% EtOAc in hexanes). MS (m/z): 424 [M+1]$^+$. $^1$H NMR (300 MHz, CDCl$_3$) δ 7.82–7.22 (m, 2H), 7.05–7.01 (m, 1H), 5.21 (d, J=7.50 Hz, 1H), 5.20–4.80 (m, 1H), 4.94 (br. t, 1H), 4.78–4.73 (m, 1H), 4.01 (t, J=9.1 Hz, 1H), 3.85–3.77 (m, 3H), 3.53–3.49 (m, 2H), 2.69–2.62 (m, 2H), 1.43–1.38 (m, 9H).

Step 7. Preparation of 1-[4-(5-aminomethyl-2-oxo-oxazolidin-3-yl)-2,6-difluoro-phenyl]-2,3-dihydro-1H-pyridin-4-one Hydrochloride.

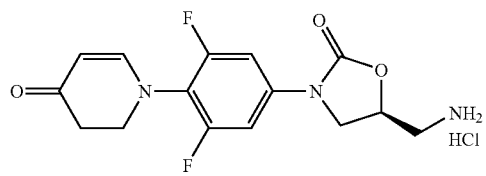

The title compound is prepared from {3-[3,5-difluoro-4-(4-oxo-3,4-dihydro-2H-pyridin-1-yl)-phenyl]-2-oxo-oxazolidin-5-ylmethyl}-carbamic acid tert-butyl ester following the method described in example 3. MS (m/z): 324 [M−HCl+H]$^+$.

Step 9. Preparation of N-{3-[3,5-difluoro-4-(4-oxo-3,4-dihydro-2H-pyridin-1-yl)-phenyl]-2-oxo-oxazolidin-5-ylmethyl}-2,2-difluoro-acetamide.

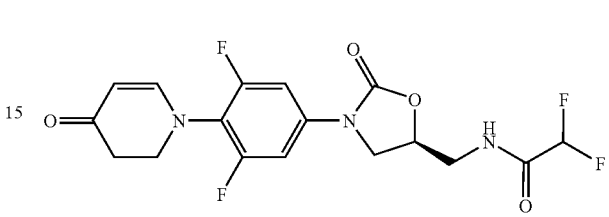

The compound is prepared from {3-[3,5-difluoro-4-(4-oxo-3,4-dihydro-2H-pyridin-1-yl)-phenyl]-2-oxo-oxazolidin-5-ylmethyl}-carbamic acid tert-butyl ester (402 mg, 0.92 mmol) and ethyl difluoroacetate (360 mg, 2.88 mmol) following the method described in example 9. The crude product is purified by silica gel column chromatography (eluent: EtOAc) to give a white solid. Yield 68 mg (18%). MS (m/z): 402 [M+1]$^+$. $^1$H NMR (300 MHz, DMSO-d$_6$): 9.16 (br. t, 1H), 7.46–7.38 (m, 3H), 6.24 (dd, J=11.0 and 14.8 Hz, 1H), 4.99 (d, J=7.4 Hz, 1H), 4.85–4.81 (m, 1H), 4.15 (t, J=9.3 Hz, 1H), 3.81–3.74 (m, 3H), 3.52 (t, J=5.5 Hz, 2H), 2.48 (m, 2H).

Example 14

Preparation of N-{3-[3,5-difluoro-4-(4-oxo-3,4-dihydro-2H-pyridin-1-yl)-phenyl]-2-oxo-oxazolidin-5-ylmethyl}-2,2-difluoro-thioacetamide

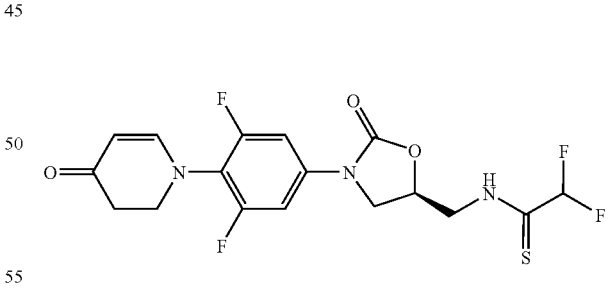

The title compound compound is prepared from {3-[3,5-difluoro-4-(4-oxo-3,4-dihydro-2H-pyridin-1-yl)-phenyl]-2-oxo-oxazolidin-5-ylmethyl}-carbamic acid tert-butyl ester (250 mg, 0.59 mmol) and difluorothioacetic acid-O-(3,3-diphenyl-propyl) ester (420 mg, 1.25 mmol) following the method described for Example 10. The crude product is purified by silica gel column chromatography (gradient 50 to 100% EtOAc in hexanes). MS (m/z): 418 [M+1]$^+$. $^1$H NMR (300 MHz, CDCl$_3$) δ11.13 (br. s, 1H), 7.46–7.38 (m, 3H), 6.49 (t, J=55.2 Hz, 1H), 5.07–4.98 (m, 2H), 4.19 (t, J=9.1 Hz), 1H), 4.02–3.76 (m, 5H).

Example 15

Preparation of 2,2-dichloro-N-{3-[3,5-difluoro-4-(4-oxo-3,4-dihydro-2H-pyridin-1-yl)-phenyl]-2-oxo-oxazolidin-5-ylmethyl}-acetamide

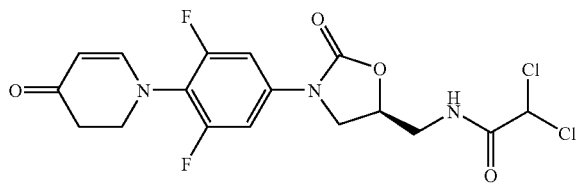

The title compound is prepared from {3-[3,5-difluoro-4-(4-oxo-3,4-dihydro-2H-pyridin-1-yl)-phenyl]-2-oxo-oxazolidin-5-ylmethyl}-carbamic acid tert-butyl ester (250 mg, 0.59 mmol) following the method described for Example 5. Purification is accomplished by silica gel chromatography (eluent: EtOAc) followed by recrystallization from MeOH. MS (m/z): 435 [M+1]$^+$. $^1$H NMR (300 MHz, DMSO-d$_6$) δ 8.96 (t, J=6.0 Hz, 1H), 7.45–7.37 (m, 3H), 6.47 (s, 1H), 7.46 (d, J=7.8 Hz), 4.86–4.81 (m, 1H), 4.15 (t, J=9.0 Hz, 1H), 3.80–3.71 (m, 3H), 3.57–3.51 (m, 2H), 2.50–2.44 (m, 2H).

Example 16

Preparation of 1-{2-fluoro-4-[(5R)-2-oxo-5-(1H-1,2,3-triazol-1-ylmethyl)-1,3-oxazolidin-3-yl]phenyl}-2,3-dihydropyridin-4(1H)-one

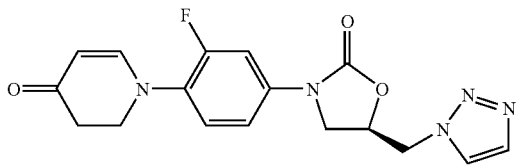

Step 1. Preparation of Preparation of [3-fluoro-4-(4-oxo-3,4-dihydro-2H-pyridin-1-yl)-phenyl]-carbamic Acid Benzyl Ester.

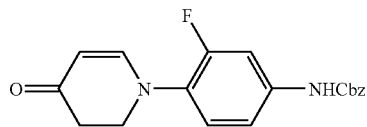

Following the procedure described in Example 8, step 5 but starting with 1-(4-amino-2-fluorophenyl)-2,3-dihydro-1H-pyridin-4-one, the titled compound is prepared.

Step 2. Preparation of 1-[(5R)-2-Fluoro-4-(5-hydroxymethyl-2-oxo-oxazolidin-3-yl)-phenyl]-2,3-dihydro-1H-pyridin-4-one.

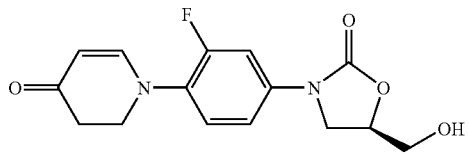

A solution of the product of step 1 above (1 g, 2.9 mmol, 1 equiv) in THF anhydrous (15 mL) is cooled down to −78° C. and lithium bis(trimethylsilyl)amide 1.0 M in THF (3.2 mL, 3.2 mmol, 1.1 equiv) is added dropwise. The reaction mixture is stired at −78° C. for 1 h. (R)-(−)-Glycidal butyrate (466 mg, 0.46 mL, 3.2 mmol, 1.1 equiv) is added dropwise and the reaction mixture is allowed to gradually warm to room temperature and is left to stir over weekend. The mixture is quenched with saturated aqueous ammonium chloride (20 mL), diluted with water (30 mL) and extracted with EtOAc (3×50 mL). The washed organics with brine are dried over (MgSO$_4$) and concentrated. The product is purified by flash chromatography on silica gel using 1–3% MeOH in DCM as eluant to give the title compound as a solid (380 mg, 1.24 mmol, 42.8%). HPLC R$_f$=4.36, MS=(M+H)$^+$=307.

Step 3. Preparation of 1-[(5R)-2-fluoro-4-(5-azidomethyl-2-oxo-oxazolidin-3-yl)-phenyl]-2,3-dihydro-1H-pyridin-4-one.

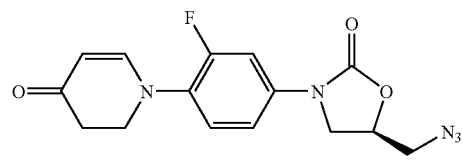

A mixture of 1-[(5R)-2-fluoro-4-(5-hydroxymethyl-2-oxo-oxazolidin-3-yl)-phenyl]-2,3-dihydro-1H-pyridin-4-one (380 mg, 1.24 mmol, 1 equiv) and TEA (251 mg, 0345 mL, 2.48 mmol, 2 equiv) in DCM (5 mL) are chilled to 0° C. and added into (dropwise) methanesulfonyl chloride (223 mg, 0.151 mL, 1.95 mmol, 1.5 equiv). Allow the mixture gradually warm to room temperature and stir for about three hours. Pour the solution into water (50 mL) and extracted with DCM (3×50 mL). The combined organics is saturated with aqueous NaHCO$_3$ (50 mL) and brine (50 mL), dried over (MgSO$_4$) and concentrated to give a viscous oily mesylate (1.24 mmol). HPLC R$_f$=4.80, MS=(M+H)$^+$=385.

The mesylate (1.24 mmol) in DMF (4 mL), is then treated with sodium azide (403 mg, 6.2 mmol, 5 Equiv) and heated at about 50 to 60° C. for 24 h. Allow the reaction mixture to cool down to room temperature, diluted with water (35 mL) and extracted with EtOAc (3×45 mL). The combined organics is washed with water (40 mL) and brine (40 ML), dried over (MgSO$_4$) and concentrated to give the title compound (265 mg, 0.80 mmol, 64.6%). HPLC R$_f$=5.10, MS=(M+H)$^+$=332.

Step 4. Preparation of 1-{2-fluoro-4-[(5R)-2-oxo-5-(1H-1,2,3-triazol-1-ylmethyl)1,3-oxazolidin-3-yl]phenyl}-2,3-dihydropyridin-4(1H)-one.

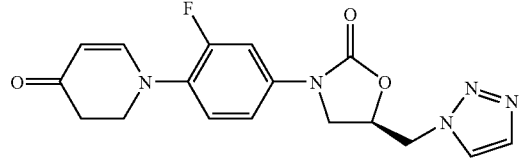

Treat a solution of azide (265 mg, 0.80 mmol, 1 equiv) in dioxane (5 mL) with bicyclo[2.2.1]hepta-2,5-diene. The mixture is slowly heated to reflux (~100° C.) and and allow the mixture being heated for about 4 houre. The reaction mixture is concentrated, purified by flash chromatography on solica gel eluting (first with 5% MeOH in EtOAc and then over a second silica gel column with 5% MeOH in DCM). Induced crystallization with ETOAc to give the title compound as a white solid (50 mg, 0.14 mmol, 17.5 MS=(M+H)$^+$=358. $^1$H NMR (300 MHz, DMSO-d$_6$) δ 8.17 (s, 1H), 7.76 (s, 1H), 7.46–7.56 (m, 3H), 7.38 (t, J=9.3 Hz, 1H), 7.27 (dd, J=9, 2.1 Hz, 1H), 5.12–5.17 (m, 1H), 4.98 (d, J=7.8 Hz, 1H), 4.83 (m, 1H), 4.24 (t, J=9.3 Hz, 1H), 3.84–3.92 (m, 3H), 2.47 (m, 2H).

Example 17

Preparation of 1-{4-[(5R)-2-oxo-5-(1H-1,2,3-triazol-1-ylmethyl)-1,3-oxazolidin-3-yl]phenyl}-2,3-dihydropyridin-4(1H)-one Following the procedure described in Example 16 and under analogous conditions, but starting with 1-(4-aminophenyl)-2,3-dihydro-1H-pyridin-4-one, the titled compound is prepared. $^1$H NMR (400 MHz, CD$_3$CN) δ 7.88 (s, 1H), 7.67 (s, 1H), 7.52 (d, J=8 Hz, 1H), 7.44 (d, J=9.2 Hz, 1H), 7.18 (d, J=9.2 Hz, 1H), overlapping 5.04–5.06 (m, 1H) and 5.04 (d, J=8 Hz, 1H), 4.74–4.76 (m, 2H), 4.18 (t, J=7.6 Hz, 2H), 3.87 (dd, J=9.2, 5.2 Hz, 1H), 2.52 (t, J=7.6 Hz, 2H).

What is claimed is:

1. A compound of formula I

I or a pharmaceutically acceptable salt thereof wherein:
A is a structure ii ii

X is
(a) NHC(=O)R$^1$, or
(b) NHC(=S)R$^1$;
R$^1$ is
(a) NH$_2$,
(b) NHC$_{1-4}$ alkyl,
(c) C$_{1-4}$ alkyl,
(d) C$_{2-4}$ alkenyl,
(e) —(CH$_2$)$_n$C(=O)C$_{1-4}$ alkyl,
(f) OC$_{1-4}$ alkyl,
(g) SC$_{1-4}$ alkyl, or
(h) (CH$_2$)$_n$C$_{3-6}$ cycloalkyl;
R$^2$ and R$^3$ are independently
(a) H,
(b) Cl,
(c) F,
(d) CH$_3$,
(e) NH$_2$, or
(f) OH;
R$^4$ is
(a) H,
(b) F,
(c) Cl,
(d) NH$_2$,
(e) OH,
(f) CN,
(g) C$_{1-4}$ alkyl,
(h) OC$_{1-4}$ alkyl,
(i) C$_{1-4}$ alkyl-W—C$_{1-4}$ alkyl, wherein W is O or S
(j) NHC$_{1-4}$ alkyl,
(k) (CH$_2$)$_n$C$_{3-6}$ cycloalkyl,
(l) C(=O)C$_{1-4}$ alkyl,
(m) OC(=O)C$_{1-4}$ alkyl,
(n) C(=O)OC$_{1-4}$ alkyl,
(o) C(=O)NHC$_{1-4}$ alkyl, or
(p) C(=O)NH$_2$;
n is 0, 1, or 2; and
at each occurance alkyl, alkenyl, or cycloalkyl is optionally substituted with 1, 2 or 3 halo.

2. A compound of claim 1 wherein X is NHC(=O)R$^1$.

3. A compound of claim 1 wherein R$^1$ is CH$_3$, CH$_2$CH$_3$, CHF$_2$, CF$_3$, or CHCl$_2$.

4. A compound of claim 1 wherein R$^2$ and R$^3$ are independently H or F.

5. A compound of claim 1 wherein R$^4$ is H.

6. A compound of claim 1 which is
N-{3-[3-fluoro-4-(4-oxo-3,4-dihydro-2H-pyridin-1-yl)-phenyl]-2-oxo-oxazolidin-5-ylmethyl}-acetamide;
N-{3-[3,5-difluoro-4-(4-oxo-3,4-dihydro-2H-pyridin-1-yl)-phenyl]-2-oxo-oxazolidin-5-ylmethyl}-acetamide;
N-{3-[3-fluoro-4-(4-oxo-3,4-dihydro-2H-pyridin-1-yl)-phenyl]-2-oxo-oxazolidin-5-ylmethyl}-difluoroacetamide;
N-{3-[3-fluoro-4-(4-oxo-3,4-dihydro-2H-pyridin-1-yl)-phenyl]-2-oxo-oxazolidin-5-ylmethyl}-propionamide;
N-{3-[3,5-difluoro-4-(4-oxo-3,4-dihydro-2H-pyridin-1-yl)-phenyl]-2-oxo-oxazolidin-5-ylmethyl}-propionamide;
2,2-dichloro-N-{3-[3-fluoro-4-(4-oxo-3,4-dihydro-2H-pyridin-1-yl)-phenyl]-2-oxo-oxazolidin-5-ylmethyl}-acetamide;
2,2-difluoro-N-{3-[3-fluoro-4-(4-oxo-3,4-dihydro-2H-pyridin-1-yl)-phenyl]-2-oxo-oxazolidin-5-ylmethyl}-thioacetamide;
{3-[3-dluoro-4-(4-oxo-3,4-dihydro-2H-pyridin-1-yl)-phenyl]-2-oxo-oxazolidin-5-ylmethyl}-carbamic acid methyl ester;
{3-[3,5-difluoro-4-(4-oxo-3,4-dihydro-2H-pyridin-1-yl)-phenyl]-2-oxo-oxazolidin-5-ylmethyl}-carbamic acid methyl ester;
{3-[2-oxo-3-[4-(4-oxo-3,4-dihydro-2H-pyridin-1-yl)-phenyl]-oxazolidin-5-ylmethyl}-carbamic acid methyl ester;
2,2-dichloro-N-{2-oxo-3-[4-(4-oxo-3,4-dihydro-2H-pyridin-1-yl)-phenyl]-oxazolidin-5-ylmethyl}-acetamide;
N-{2-dxo-3-[4-(4-oxo-3,4-dihydro-2H-pyridin-1-yl)-phenyl]-oxazolidin-5-ylmethyl}-acetamide;
2,2-difluoro-N-{2-oxo-3-[4-(4-oxo-3,4-dihydro-2H-pyridin-1-yl)-phenyl]-oxazolidin-5-ylmethyl}-thioacetamide;
N-{2-dxo-3-[4-(4-oxo-3,4-dihydro-2H-pyridin-1-yl)-phenyl]-oxazolidin-5-ylmethyl}-propionamide;

N-{3-[3,5-difluoro-4-(4-oxo-3,4-dihydro-2H-pyridin-1-yl)-phenyl]-2-oxo-oxazolidin-5-ylmethyl}-2,2-difluoro-acetamide;

N-{3-[3,5-difluoro-4-(4-oxo-3,4-dihydro-2H-pyridin-1-yl)-phenyl]-2-oxo-oxazolidin-5-ylmethyl}-2,2-difluoro-thioacetamide;

N-{3-[3-fluoro-4-(4-oxo-3,4-dihydro-2H-pyridin-1-yl)-phenyl]-2-oxo-oxazolidin-5-ylmethyl}-2,2-difluoro-thioacetamide;

2,2-dichloro-N-{3-[3,5-difluoro-4-(4-oxo-3,4-dihydro-2H-pyridin-1-yl)-phenyl]-2-oxo-oxazolidin-5-ylmethyl}-acetamide;

2-chloro-2-fluoro-N-({(5S)-3-[3-fluoro-4-(4-oxo-3,4-dihydropyridin-1(2H)-yl)phenyl]-2-oxo-1,3-oxazolidin-5-yl}methyl)acetamide;

N-({(5S)-3-[3-fluoro-4-(4-oxo-3,4-dihydropyridin-1(2H)-yl)phenyl]-2-oxo-1,3-oxazolidin-5-yl}methyl)cyclopropanecarboxamide;

N-({(5S)-3-[3-fluoro-4-(4-oxo-3,4-dihydropyridin-1(2H)-yl)phenyl]-2-oxo-1,3-oxazolidin-5-yl}methyl)-3-oxobutanamide;

(2E)-3-{4-[(E)-(hydroxyimino)methyl]phenyl}-N-({(5S)-2-oxo-3-[4-(4-oxo-3,4-dihydropyridin-1(2H)-yl)phenyl]-1,3-oxazolidin-5-yl}methyl)prop-2-enamide;
or (2E)-N-({(5S)-3-[3-fluoro-4-(4-oxo-3,4-dihydropyridin-1(2H)-yl)phenyl]-2-oxo-1,3-oxazolidin-5-yl}methyl)-3-{4-[(E)-(hydroxyimino)methyl]phenyl}prop-2-enamide.

7. A pharmaceutical composition comprising a compound of formula I or a pharmaceutically acceptable salt thereof, and a pharmaceutically acceptable carrier.

8. A method for the treatment of bacterial infections in mammals comprising administration of an effective amount of compound of claim 1 to said mammal.

9. The method of claim 8 wherein said compound is administered to the mammal orally, parenterally, transdermally, or topically in a pharmaceutical composition.

10. The method of claim 8 wherein said compound is administered in an amount of from about 0.1 to about 400 mg/kg of body weight/day.

11. The method of claim 8 wherein said compound is administered in an amount of from about 1 to about 50 mg/kg of body weight/day.

* * * * *